US010221216B2

(12) United States Patent
Ly et al.

(10) Patent No.: US 10,221,216 B2
(45) Date of Patent: Mar. 5, 2019

(54) TEMPLATE-DIRECTED γPNA SYNTHESIS PROCESS AND γPNA TARGETING COMPOUNDS

(71) Applicant: Carnegie Mellon University, Pittsburgh, PA (US)

(72) Inventors: Danith H. Ly, Pittsburgh, PA (US); Raman Bahal, Hamden, CT (US); Arunava Manna, Pittsburgh, PA (US); Dinesh Chandra Bhunia, Pittsburgh, PA (US); Rapireddy Srinivas, Westborough, MA (US); Yidan Cong, Gaithersburg, MD (US)

(73) Assignee: Carnegie Mellon University, Pittsburgh, PA (US)

( * ) Notice: Subject to any disclaimer, the term of this patent is extended or adjusted under 35 U.S.C. 154(b) by 339 days.

(21) Appl. No.: 14/782,448

(22) PCT Filed: Apr. 11, 2014

(86) PCT No.: PCT/US2014/033814
§ 371 (c)(1),
(2) Date: Oct. 5, 2015

(87) PCT Pub. No.: WO2014/169216
PCT Pub. Date: Oct. 16, 2014

(65) Prior Publication Data
US 2016/0083433 A1 Mar. 24, 2016

Related U.S. Application Data

(60) Provisional application No. 61/853,758, filed on Apr. 11, 2013.

(51) Int. Cl.
| *C07H 21/00* | (2006.01) |
| *C07K 14/00* | (2006.01) |
| *C12Q 1/6806* | (2018.01) |
| *C07K 7/02* | (2006.01) |
| *C12N 15/87* | (2006.01) |

(52) U.S. Cl.
CPC .............. *C07K 14/003* (2013.01); *C07K 7/02* (2013.01); *C12N 15/87* (2013.01); *C12Q 1/6806* (2013.01)

(58) Field of Classification Search
CPC .................................................. C07K 14/003
USPC ........................................................ 536/23.1
See application file for complete search history.

(56) References Cited

U.S. PATENT DOCUMENTS

| 5,217,866 A | 6/1993 | Summerton et al. |
| 6,355,726 B1 | 3/2002 | Doemling et al. |
| 8,053,212 B1 | 11/2011 | Benner |
| 8,389,703 B1 | 3/2013 | Benner et al. |
| 8,653,254 B2 | 2/2014 | Umemoto et al. |
| 2002/0188101 A1* | 12/2002 | Neilsen ................ A61K 9/1272 530/324 |
| 2005/0009041 A1 | 1/2005 | Buchardt et al. |
| 2006/0160751 A1 | 7/2006 | McGuire |
| 2011/0028337 A1 | 2/2011 | Bradley et al. |

FOREIGN PATENT DOCUMENTS

| WO | 2004024757 A2 | 3/2004 |
| WO | 2012138955 A2 | 10/2012 |

OTHER PUBLICATIONS

Stratagene Catalog p. 39, 1988.*
Sugiyama et al., "Chiral Peptide Nucleic Acids with a Substituent in the N-(2-Aminoethy)glycine Backbone", Molecules, 2013, vol. 18, pp. 287-310.
Tackett et al., "Non-Watson-Crick interactactions between PNA and DNA inhibit the ATPase activity of bacteriophage T4 Dda helicase", Nucleic Acids Research, 2002, vol. 30:4, pp. 950-957.
Tedeschi et al., "Synthesis of new chiral PNAs bearing a dipeptide-mimic monomer with two lysine-derived stereogenic centres", Tetrahedron Letters, 2005, vol. 46, pp. 8395-8399.
Theimer et al., "Structure of the Human Telomerase RNA Pseudoknot Reveals Conserved Tertiary Interactions Essential for Function", Molecular Cell, 2005, vol. 17, pp. 671-682.
Thurner et al., "Conserved RNA secondary structures in Flaviviridae genomes", Journal of General Virology, 2004, vol. 85, pp. 1113-1124.
Tomac et al., "Ionic Effects on the Stability and Conformation of Peptide Nucleic Acid Complexes", Journal of the American Chemical Society, 1996, vol. 118, pp. 5544-5552.
Wan et al., "Understanding the transcriptome through RNA structure", Nature Review Genetics, 2011, vol. 12, pp. 641-655.
Watts et al., "Architecture and secondary structure of an entire HIV-1 RNA genome", Nature, 2009, vol. 460, pp. 711-719.
Wei et al., "Complex shapes self-assembled from single-stranded DNA tiles", Nature, 2012, vol. 485, pp. 623-627.
Wengel, "Synthesis of 3'-C- and 4'-C-Branched Oligodeoxynucleotides and the Development of Locked Nucleic Acid (LNA)", Accounts of Chemical Research, 1999, vol. 32:4, pp. 301-310.
Wimberly et al., "Structure of the 30S ribososmal subunit", Nature, 2000, vol. 407, pp. 327-339.
Winssinger, "Nucleic Acid-programmed Assemblies: Translating Instruction into Function in Chemical Biology", Chimia, 2013, vol. 67:5, pp. 340-348.
Wittung et al., "DNA-like double helix formed by peptide nucleic acid", Nature, 1994, vol. 368. pp. 561-563.
Wittung et al., "Induced Chirality in PNA-PNA Duplexes", Journal of the American Chemical Society, 1995, vol. 117:41, pp. 10167-10173.
Wu et al., "Synthesis of chiral peptide nucleic acids using Fmoc chemistry", Tetrahedron, 2001, vol. 57, pp. 8107-8113.

(Continued)

*Primary Examiner* — Jezia Riley
(74) *Attorney, Agent, or Firm* — The Webb Law Firm

(57) ABSTRACT

Described herein are recognition modules that bind specifically to a template nucleic acid and which ligate together in a reducing environment to produce a gamma peptide nucleic acid (γPNA) oligomer. Also provided are methods of synthesizing a γPNA oligomer on a template using the recognition modules.

57 Claims, 17 Drawing Sheets

Specification includes a Sequence Listing.

(56) References Cited

OTHER PUBLICATIONS

Yan et al., "DNA-Templated Self-Assembly of Protein Arrays and Highly Conductive Nanowires", Science, 2003, vol. 301, pp. 1882-1884.
Yang et al., "Light-switching excimer probes for rapid protein monitoring in complex biological fluids", PNAS, 2005, vol. 102:48, pp. 17278-17283.
Yeh et al., "Crystal Structure of Chiral gammaPNA with Complementary DNA Strand: Insights into the Stability and Specificity of Recognition and Conformational Preorganization", Journal of the American Chemical Society, 2010, vol. 132:31, pp. 10717-10727.
Yurke et al., "A DNA-fuelled molecular machine made of DNA", Nature, 2000, vol. 406, pp. 605-608.
Zhang et al., "Dynamic DNA nanotechnology using strand displacement reactions", Nature Chemistry, 2011, vol. 3, pp. 103-113.
Zhou et al., "Novel Binding and Efficient Cellular Uptake of Guanidine-Based Peptide Nucleic Acids (GPNA)", Journal of the American Chemical Society, 2003, vol. 125, pp. 6878-6879.
Adleman, "Molecular Computation of Solution to Combinatorial Problems", Science, 1994, vol. 266, pp. 1021-1024.
Aldaye et al., "Assembling Materials with DNA as the Guide", Science, 2008, vol. 321, pp. 1795-1799.
Ashley, "Modeling, Synthesis, and Hybridization Properties of (L)-Ribonucleic Acid", Journal of the American Chemical Society, 1992, vol. 114:25, pp. 9731-9736.
Avitabile et al., "γsulphate PNA (PNA S): Highly Selective DNA Binding Molecule Showing Promising Antigene Activity", Peptide Nucleic Acid analogues, 2012, vol. 7:5, pp. 1-10.
Bahal et al., "Sequence-Unrestricted, Watson-Crick Recognition of Double Helical B-DNA by (R)-MiniPEG-γPNAs", ChemBioChem, 2012 vol. 13, pp. 56-60.
Bahal et al., "Single-Stranded γPNAs for In Vivo Site-Specific Genome Editing via Watson-Crick Recognition", Current Gene Therapy, 2014, vol. 15, pp. 331-342.
Ban et al., "The Complete Atomic Structure of the Large Ribosomal Subunit at 2.4 Å Resolution", Science, 2000, vol. 289, pp. 905-920.
Bath et al., "DNA nanomachines", Nature Nanotechnology, 2007, vol. 2, pp. 275-284.
Beck et al., "Artificial DNA: methods and applications", 2003, CRC Press, Boca Raton, vol. 2003 pp. 91-115.
Berry et al., "Crystal structure of the HCV IRES central domain reveals strategy for start-codon positioning", Structure, 2011, vol. 19, pp. 1456-1466.
Braasch et al., "Synthesis, Analysis, Purification, and Intracellular Delivery of Peptide Nucleic Acids", Methods, 2001, vol. 23, pp. 97-107.
Butcher et al., "The Molecular Interactions That Stabilize RNA Tertiary Structure: RNA Motifs, Patterns, and Networks", Accounts of Chem. Res., 2011, vol. 44:12, pp. 1302-1311.
Chen et al., "Synthesis from DNA of a molecule with the connectivity of a cube", Letters to Nature, 1991, vol. 350, pp. 631-633.
Chen, "Expanding the Rule Set of DNA Circuitry with Associative Toehold Activation, Journal of the American Chemical Society", 2012, vol. 134, pp. 263-271.
Chin et al., "Correction of a splice-site mutation in the beta-globin gene stimulated by triplex-forming peptide nucleic acids," PNAS, 2008, vol. 15:36, p. 13514-13519.
Choi et al., "Programmable in situ amplification for multiplexed imaging of mRNA expression", Nature Biotechnology, 2010, vol. 28:11, pp. 1208-1214.
Choi et al., "Next-Generation in Situ Hybridization Chain Reaction: Higher Gain, Lower Cost, Greater Durability", ACS Nano, 2014. vol. 8:5. pp. 4284-4294.
Costantino et al., "tRNA-mRNA mimicry drives translation initiation from a viral IRES", Nat. Struct. Mol. Biol., 2008, vol. 15:1, pp. 57-64.
Dawson et al., "Synthesis of Proteins by Native Chemical Ligation", Science, 1994, vol. 266:5186, pp. 776-779.

De Costa et al., "Evaluating the Effect of Ionic Strength on Duplex Stability for PNA Having Negatively or Positively Charged Side Chains", PLOS ONE, 2013, vol. 8:3, pp. 1-8.
De Francesco et al., "Challenges and successes in developing new therapies for hepatitis C", Nature, 2005, 436:18, pp. 953-960.
Delebecque et al., "Organization of Intracellular Reactions with Rationally Designed RNA Assemblies", Science, 2011, vol. 333, pp. 470-474.
Demidov et al., "Stability of peptide nucleic in human serum and cellular extracts", Biochemical Pharacology, 1994, vol. 48:6, pp. 1310-1313.
Dezhenkov et al., "Synthesis of anionic peptide nucleic acid oligomers including γ-carboxyethyl thymine monomers", Mendeleev Commun., 2015, vol. 25, pp. 47-48.
Dibrov et al., "Structure of a hepatitis C virus RNA domain in complex with a translation inhibitor reveals a binding mode reminiscent of riboswitches", PNAS, 2012, vol. 109:14, pp. 5223-5228.
Dietz et al., "Folding DNA into Twisted and Curved Nanoscale Shapes", Science, 2009, vol. 325. pp. 725-730.
Dirks et al., "Triggered amplification by hybridization chain reaction", PNAS, 2004, vol. 101:43, pp. 15275-15278.
Dose et al., "Convergent Synthesis of Peptide Nucleic Acids by Native Chemical Ligation", Organic Letters, 2005, vol. 7:20, pp. 4365-4368.
Doudna, "Structural genomics of RNA", Nature Structural Biology, 2000, pp. 954-956.
Douglas et al., "A Logic-Gated Nanorobot for Targeted Transport of Molecular Payloads", Science, 2012, vol. 335, pp. 831-834.
Dragulescu-Andrasi et al.; "A Simple Gamma-Backbone Modification Preorganizes Peptide Nucleic Acid into a Helical Structure", JACS, 2006, vol. 128:31, 10258-10267.
Dueholm et al., "Synthesis of Peptide Nucleic Acid Monomers Containing the Four Natural Nucleobases: Thymine, Cytosine, Adenine, and Guanine and Their Oligomerization", Journal of Organic Chemistry, 1994, vol. 59:19, pp. 5767-5773.
Englund et al., "Synthesis of γ-Substituted Peptide Nucleic Acids: A New Place to Attach Fluorophores without Affecting DNA Binding", Organic Letters, 2005, vol. 7:16, pp. 3465-3467.
Falkiewicz et al., "Synthesis of achiral and chiral peptide nucleic acid (PNA) monomers using Mitsunobu reaction", Tetrahedron, 2001, vol. 57, pp. 7909-7917.
Fischer, Ber. Dtsch. Chem. Ges., 1894, vol. 27, pp. 2985-2993.
Frezza et al., "Modular Multi-Level Circuits from Immobilized DNA-Based Logic Gates", Journal of American Chemical Society, 2007. vol. 129, pp. 14875-14879.
Fujimori et al., "Enantio-DNA Recognizes Complementary RNA but Not Complementary DNA", Journal of American Chemical Society, 1990, vol. 112, pp. 7436-7438.
Genot et al., "Reversible Logic Circuits Made of DNA", Journal of American Chemical Society, 2011, vol. 133, pp. 20080-20083.
Gerling et al., "Dynamic DNA devices and assemblies formed by shape-complementary, non-base pairing 3D components", Science, 2015, vol. 347:6229, pp. 1446-1452.
Hameed, "DNA Computation Based Approach for Enhanced Computing Power", Int. J. Emerg. Sci., 2011, vol. 1:1, pp. 31-37.
Han et al., "DNA Origami with Complex Curvatures in Three-Dimensional Space", Science, 2011, vol. 332, pp. 342-346.
He et al., "Strand-Invasion of Extended, Mixed-Sequence B-DNA by gammaPNAs", Journal of American Chemical Society, 2009, vol. 131:34, pp. 12088-12090.
Hirao et al., "Natural versus Artificial Creation of Base Pairs in DNA: Origin of Nucleobases from the Perspectives of Unnatural Base Pair Studies", Accounts of Chemical Research, 2012, vol. 45:12, pp. 2055-2065.
Huang et al., "Preparation and Determination of Optical Purity of γ-Lysine Modified Peptide Nucleic Acid Analogues", Archives of Pharmacal Research, 2012, vol. 35:3, pp. 517-522.
Immordino et al., "Stealth liposomes: review of the basic science, rationale, and clinical applications, existing and potential", International Journal of Nanomedicine, 2006, vol. 1:3, pp. 297-316.
Janowski et al., "Inhibiting transcription of chromosomal DNA with antigene peptide nucleic acids", Nature Chemical Biology, 2005, vol. 1:4, pp. 210-215.

(56) References Cited

OTHER PUBLICATIONS

Johnston et al., "An HIV Vaccine-Challenges and Prospects", New England Journal of Medicine, 2008, vol. 359:9 pp. 888-890.
Jones et al., "Programmable materials and the nature of the DNA bond", Science, 2015, vol. 347:6224, pp. 840-853.
Kadhane et al., "Strong coupling between adenine nucleobases in DNA single strands revealed by circular dichroism using synchrotron radiation", Physical Review, 2008, pp. 021901-1-021901-4.
Ke et al., "Three-Dimensional Structures Self-Assembled from DNA Bricks", Science, 2012, vol. 338, pp. 1177-1183.
Kleiner et al., "DNA-Templated Polymerization of Side-Chain-Functionalized Peptide Nucleic Acid Aldehydes", Journal of American Chemical Society, 2008, vol. 130, pp. 4646-4659.
Konrad et al., "Synthese and Eigenschaften von 2.4-Diamino-6-und-7-oxo-dihydropteridinen", Chem. Ber., 1970, vol. 103, pp. 735-744.
Koppelhus et al., "Cell-Dependent Differential Cellular Uptake of PNA, Peptides, and PNA-Peptide Conjugates", Antisense & Nucleic Acid Drug Development, 2002, vol. 12, pp. 51-63.
Kosynkina et al., "A Convenient Synthesis of Chiral Peptide Nucleic Acid (PNA) Monomers", Tetrahedron Letters, 1994, vol. 35:29, pp. 5173-5176.
Kuhn et al., "Hybridization of DNA and PNA Molecular Beacons to Single-Stranded and Double-Stranded DNA Targets", Journal of American Chemical Society, 2002, vol. 124:6, pp. 1097-1103.
Kumar et al., "Conformationally Constrained PNA Analogues: Structural Evolution toward DNA/RNA Binding Selectivity", Accounts of Chemical Research, 2005, vol. 38:5, pp. 404-412.
Kuzyk et al., "DNA-based self-assembly of chiral plasmonic nanostructures with tailored optical response", Nature, 2012, vol. 483, pp. 311-314.
Li et al., "Controlled assembly of dendrimer-like DNA", Nature Materials, 2004, vol. 3, pp. 38-42.
Li et al., "DNA-Templated Organic Synthesis: Nature's Strategy for Controlling Chemical Reactivity Applied to Synthetic Molecules", Angewandte Chemie International Edition, 2004, vol. 43, pp. 4848-4870.
Liedl et al., "DNA-based nanodevices", Nanotoday, 2007, vol. 2:2, pp. 36-41.
Lin et al., "Whole Genome Shotgun Optical Mapping of Deinococcus Radiodurans", Science, 1999, vol. 285, pp. 1558-1562.
Lund et al., "Molecular robots guided by prescriptive landscapes", Nature, 2010, vol. 465, pp. 206-210.
Manna et al. "Synthesis of optically pure γPNA monomers: a comparative study", Tetrahedron, 2015, vol. 71, pp. 3507-3514.
Michaelis et al., "Amplification by nucleic acid-templated reactions", Organic & Biomolecular Chemistry, 2014, vol. 12, pp. 2821-2833.
Mir, "Sequencing Genomes: From Individuals to Populations", Briefings in Functional Genomics and Proteomics., 2009, vol. 8:5, pp. 367-378.
Mitra et al., "Aminomethylene Peptide Nucleic Acid (am-PNA): Synthesis, Regio-/Stereospecific DNA Binding, and Differential Cell Uptake of (α/γ,R/S)am-PNA Analogues", The Journal of Organic Chemistry, 2012, vol. 77, pp. 5696-5704.
Moradpour et al., "Replication of hepatitis C virus," Nature Reviews Microbiology, 2007, vol. 5, pp. 453-463.
Morens et al., "The challenge of emerging and re-emerging infectious diseases", Nature, 2004, vol. 430, pp. 242-249 and corrections, Nature, 2010, vol. 463, pp. 122.
Nielsen et al., "Sequence-Selective Recognition of DNA by Strand Displacement with a Thymine-Substituted Polyamide", Science, 1991, vol. 254, pp. 1497-1500.
Nielsen, "Peptide Nucleic Acid. A Molecule with Two Identities", Acc. Chem. Res., 1999, vol. 32, pp. 624-630.
Nielsen, "Addressing the challenges of cellular delivery and bioavailability of peptidenucleic acids (PNA)", Quarterly Reviews of Biophysics, 2005, vol. 38:4, pp. 345-350.
Nissen et al., "RNA tertiary interactions in the large ribosomal subunit: The A-minor motif", PNAS, 2001, vol. 98:9, pp. 4899-4903.
Niu et al., "AApeptides as a new class of antimicrobial agents", Organic & Biomolecular Chemistry, 2013, vol. 11, pp. 4283-4290.
Noller, "RNA Structure: Reading the Ribosome", Science, 2005, vol. 309, pp. 1508-1514.
Oh et al., "Excimer-Based Peptide Beacons: A Convenient Experimental Approach for Monitoring Polypeptide-Protein and Polypeptide-Oligonucleotide Interactions", Journal of American Chemical Society, 2006, vol. 128, pp. 14018-14019.
Omabegho et al., "A Bipedal DNA Brownian Motor with Coordinated Legs", Science, 2009, vol. 324, pp. 67-71.
Pfingsten et al., "Structural Basis for Ribosome Recruitment and Manipulation by a Viral IRES RNA", Science, 2006, vol. 314:5804, pp. 1450-1454.
Piccirilli et al., "Enzymatic incorporation of a new base pair into DNA and RNA extends the genetic alphabet", Nature, 1990, vol. 343, pp. 33-37.
Pinheiro et al., "Challenges and opportunities for structural DNA nanotechnology", Nature Nanotechnology, 2011, vol. 6:12, pp. 763-772.
Poehlsgaard et al., "The Bacterial Ribosome as a Target for Antibiotics", Nature Reviews Microbiology, 2005, vol. 3, pp. 870-881.
Qian et al., "Scaling Up Digital Circuit Computation with DNA Strand Displacement Cascades", Science, 2011, vol. 332, pp. 1196-1201.
Rajwanshi et al., "LNA stereoisomers: xylo-LNA (β-D-xylo configured locked nucleic acid) and α-L-LNA (α-L-ribo configured locked nucleic acid)", Chem. Commun, 1999, pp. 1395-1396.
Ranasinghe et al., "Linear fluorescent oligonucleotide probes with an acridine quencher generate a signal upon hybridization", Chem. Commun., 2001, pp. 1480-1481.
Rapireddy et al., "Strand Invasion of Mixed-Sequence B-DNA by Acridine-Linked, gamma-Peptide Nucleic Acid (gamma-PNA)", JACS, 2007, vol. 129, pp. 15596-15600.
Rapireddy et al., "Strand-Invasion of Mixed-Sequence, Double-Helical B-DNA by gamma-Peptide Nucleic Acids Containing G-Clamp Nucelobases under Physiological Conditions," Biochemistry, 2011, vol. 50, pp. 3913-3918.
Ratilainen et al., "Hybridization of Peptide Nucleic Acid", Biochemistry, 1998, vol. 37, pp. 12331-12342.
Ratilainen et al., "Thermodynamics of Sequence-Specific Binding of PNA to DNA", Biochemistry, 2000, vol. 39, pp. 7781-7791.
Rothemund, "Folding DNA to create nanoscale shapes and patterns", Nature, 2006, vol. 440, pp. 297-302.
Sahoo et al., "Pyrene Excimer Fluorescence: A Spatially Sensitive Probe to Monitor Lipid-Induced Helical Rearrangement of Apolipophorin III", Biochemistry, 2000, vol. 39, pp. 6594-6601.
Sahu et al., "Synthesis of Conformationally Preorganized and Cell-Permeable Guanidine-Based gamma-Peptide Nucleic Acids (gammaGPNAs)", J. Org. Chem., 2009, vol. 74, pp. 1509-1516.
Sahu et al., "Synthesis and Characterization of Conformationally Preorganized, MiniPEG-Containing γPNAs with Superior Hbridization Properties and Water Solubility", J. Org. Chem., 2011, vol. 76:14, pp. 5614-5627.
Seelig et al., "Enzyme-Free Nucleic Acid Logic Circuits", Science, 2006, vol. 314, pp. 1585-1588.
Seitz, "Solid-Phase Synthesis of Doubly Labeled Peptide Nucleic Acids as Probes for the Real-Time Detection of Hybridization", Angewandte Chemie International Edition, 2000, vol. 39:18, pp. 3249-3252.
Serpell et al., "Precision Polymers and 3D DNA Nanostructures: Emergent Assemblies from New Parameter Space", Journal of the American Chemical Society, 2014, vol. 136, pp. 15767-15774.
Severcan et al., "A polyhedron made of tRNAs", Nature Chemistry, 2010, vol. 2, pp. 772-779.
Sforza et al., "Chiral Peptide Nucleic Acids (PNAs):Helix Handedness and DNA Recognition", European Journal of Organic Chemistry, 1999, pp. 197-204.
Silverman et al., "Detecting RNA and DNA with Templated Chemical Reactions", Chemical Reviews, 2006, vol. 106, pp. 3775-3789.

(56) References Cited

OTHER PUBLICATIONS

Singer et al., "Electronic Barcoding of a Viral Gene at the Single-Molecule Level", Nano Letters, 2012, vol. 12, pp. 1722-1728.
Smalley et al., "Fluorescence of covalently attached pyrene as a general RNA folding probe", Nucleic Acids Research, 2006, vol. 34:1, pp. 152-166.
Stanzle et al., "Fifteen Years of Cell-Penetrating, Guanidinium-Rich Molecular Transporters: Basic Sciene", Accounts of Chemical Research, 2013, vol. 46:12, pp. 2944-2954.

* cited by examiner

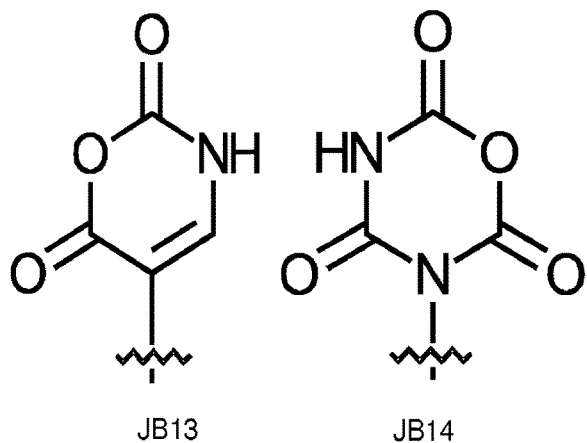
JB13  JB14
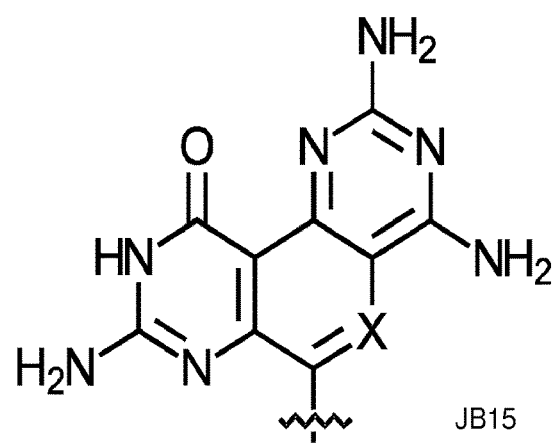
JB15
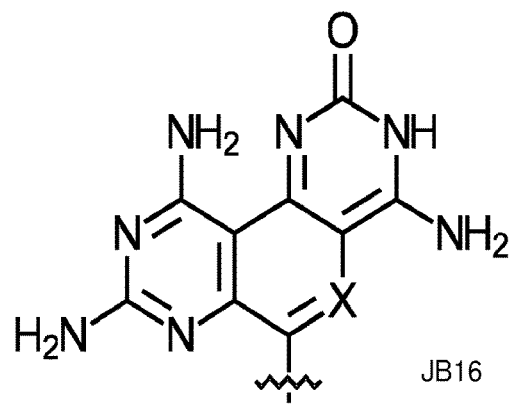
JB16
*Fig. 4B-3*

Scheme 2

SEQUENCE LISTING

```
<160> NUMBER OF SEQ ID NOS: 1

<210> SEQ ID NO 1
<211> LENGTH: 12
<212> TYPE: RNA
<213> ORGANISM: Artificial Sequence
<220> FEATURE:
<223> OTHER INFORMATION: T12 Target RNA

<400> SEQUENCE: 1
cugcugcugc ug                                                          12
```

TEMPLATE-DIRECTED γPNA SYNTHESIS PROCESS AND γPNA TARGETING COMPOUNDS

CROSS REFERENCE TO RELATED APPLICATIONS

This application is a national phase of International Application No. PCT/US2014/033814 filed Apr. 11, 2014, and claims the benefit of U.S. Provisional Application No. 61/853,758 filed Apr. 11, 2013, each of which is incorporated herein by reference in its entirety.

STATEMENT REGARDING FEDERAL FUNDING

This invention was made with government support under Grant No. CHE-1012467 awarded by the National Science Foundation. The government has certain rights in this invention.

BACKGROUND

1. Field of the Invention

Described herein are methods of binding nucleic acids having repeating elements and compositions, particularly γPNA (gamma peptide nucleic acid) compositions, useful in carrying out those methods.

2. Description of the Related Art

For most organisms, the genetic information is encoded in double-stranded DNA in the form of Watson-Crick base-pairing—in which adenine (A) pairs with thymine (T) and cytosine (C) with guanine (G). Depending on which set of this genetic information is decoded through transcription and translation, the developmental program and physiological status will be determined. Development of molecules that can be tailor-designed to bind sequence-specifically to any part of this genetic biopolymer, thereby enabling the control of the flow of genetic information and assessment and manipulation of the genome's structures and functions, is important for biological and biomedical research in the effort to unravel the molecular basis of life, including molecular tools for basic research in biology. This effort is also important for medicinal and therapeutic applications for the treatment and detection of genetic diseases.

Compared to proteins, RNA molecules are easier to target because they are made up of just four building blocks (A, C, G, U), whose interactions are defined by the well-established rules of Watson-Crick base-pairing. Compared to standard, double-stranded DNA (or RNA), the secondary structures of RNA are generally thermodynamically less stable and, thus, energetically less demanding for binding because, in addition to being canonical (perfectly-matched) base-pairs, many of them are noncanonical (mismatched) and contain single-stranded loops, bulges, and junctions. The presence of these local interacting domains is essential for 'tertiary' interactions and assembly of the secondary structures into compact three-dimensional shapes. As such, slight variations in the interaction patterns or bonding strengths within these regions will have a profound effect on the overall three-dimensional folding patterns of RNA. Thus, molecules that can be used to modulate RNA interactions and thereby interfere with the RNA folding behaviors are important as molecular tools for assessing RNA functions, as well as therapeutic and diagnostic reagents.

RNA-RNA and RNA-protein interactions play key roles in gene regulation, including replication, translation, folding and packaging. The ability to selectively bind to these perturbed regions within the secondary structures of RNA is important in manipulating their physiological functions.

SUMMARY OF THE INVENTION

The methods and compositions described herein overcome three major hurdles presently facing conventional antisense and antigene approaches. A first hurdle concerns the scale and cost of oligonucleotide synthesis. Since oligonucleotides are traditionally synthesized in a step-wise fashion on solid-support, it is difficult to scale up the production. This translates to high-cost and unmet demand for oligonucleotide therapeutics. The methods and compositions described herein overcome this challenge because the recognition modules are relatively small in size, 3 to 8 nucleotides in length—bordering the molecular weights of small molecules and biomimetics. The compounds described herein can be produced in large scales using convergent, solution-phase synthesis methods, which would translate to lower production costs and greater accessibility to these materials for treatment.

A second hurdle concerns cellular delivery—specifically how to get these nucleic acid probes across the lipid-bilayer of cell membrane and into the cytoplasm and nucleus of the target cells. Most oligonucleotides are not permeable to the cell-membrane due to of their relatively large molecular weight. Their delivery into cells would require the aid of transfecting reagents, or mechanical or electrical transduction. While these approaches have been successfully used to transport oligonucleotides and other macromolecules into cells, they are limited to small scale-up, in vitro (tissue culture) experimental setups. In vivo, systemic delivery (a requirement for treatment of genetic and most infectious diseases) remains an issue, especially for diseases of the central nervous system. The present invention overcomes this limitation because of the reduced size of the recognition modules and flexibility in the chemical modifications. The fact that they are relatively small in size, they are taken-up more readily by cells and more permeable to the nuclear membrane. Further, because of their synthetic flexibility, in that any chemical group can be incorporated in the backbone of γPNAs, these recognition modules can be easily modified with specific chemical functionalities to promote cellular uptake and systemic delivery. This aspect has already been demonstrated by us.

The third hurdle concerns nonspecific binding and cytotoxic effects. When introduced into a cell, a naked piece of oligonucleotide 10-30 nt in length, synthetic or otherwise, would bind not only to its designated target but also a slew of other DNA or RNA regions with related sequences. Such nonspecific binding would trap the probe, preventing it from freely diffusing and searching for and binding to its target. A reduction in the effective concentration of the probe, due to nonspecific binding, would lead to a reduction in the efficacy. Moreover, such nonspecific binding could also lead to cytotoxic effects, as the result of misregulation of gene expression and/or perturbation of the function of other key proteins. Nonspecific binding, in fact, has been attributed as the main cause of side-effects of oligonucleotide therapeutics (as well as small molecule drugs), and presently there is no solution in sight. The present invention overcomes this limitation by taking advantage of the weak interaction between the short recognition module (typically 3 to 8 nt in length) and the target. This weak, 'kissing' interaction permits the module to freely diffuse in the intracellular environment in search for its target. Its designated target, in this case, differs from the 'random,' 'single-binding site' hit in that it contains repeated sequence element, which enables the module to assemble next to one another in a cooperative manner through adjacent base stacking and commence 'native chemical ligation' reaction to form a series of extended oligomers of varying lengths.

Also, the fact that the oligomers described herein are relatively small in size, they can be manufactured in large quantity and more cheaply using solution-phase methodology, and are more readily taken-up by cells. They are especially appealing for targeting rapidly evolving sites, such as those associated with the pathology of cancer, bacterial and viral infection, because their recognition scheme is modular in nature and could be readily modified to match the newly emerged sequence at will. This is a niche that is not currently fulfilled by small-molecules drugs, or traditional antisense or antigene targeting approach.

Presently there are a number of genetic diseases with many of them associated with unstable repeat expansion, for which there are no effective treatments or cure and illustrated in Table A. A major effort has been devoted in the last few decades towards developing and screening chemical libraries and natural product extracts for molecules that bind selectively to these repeated elements and reverse their pathogenic function. Thus far, no such molecules have been found. The challenge is that the target, in this case DNA or RNA, is monotonous in the three-dimensional architecture in comparison to proteins. This makes it difficult for small molecules to discriminate a particular site from a sea of other DNA or RNA sequences.

According to one embodiment of the invention, a method of producing γPNA oligomers is provided. The method comprises contacting a template nucleic acid in a reducing environment, such as one created by a reducing agent, with a plurality of recognition modules of Formula 1,

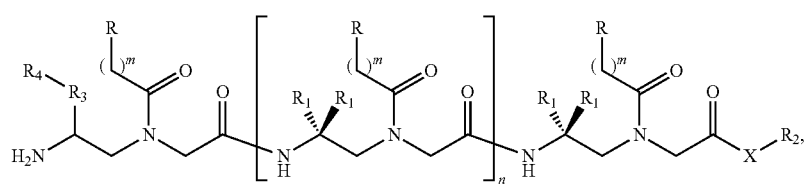

(1)

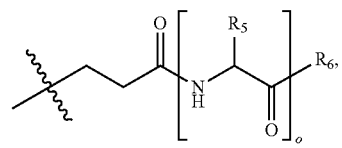

where o is 1-20, R5s are each independently an amino acid side chain and R6 is —OH or $NH_2$; R3 is $(C_1-C_{10})$ divalent hydrocarbon or $(C_1-C_{10})$ divalent hydrocarbon substituted with one or more N or O moieties, such as —O—, —OH, —C(O)—, —NH—, —$NH_2$, —C(O)NH—; R4 is —OH, —SH or a disulfide protecting group; and Rs for each of the plurality of recognition modules each independently are nucleobases producing a sequence of nucleobases complementary to a target sequence of nucleobases in the template nucleic acid so that each of the plurality of recognition modules bind to the target sequence of nucleobases on the template nucleic acid and ligate to each other. In one embodiment, R4 has the structure —SH, —OH, or —S—R7, where R7 is one or more amino acid residues, an amino acid side chain, linear, branched or hetero-substituted $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl $(C_1-C_6)$alkylene, $(C_3-C_8)$cycloalkyl$(C_1-C_6)$alkylene. In one embodiment, R1 are amino acid side chains. In another embodiment, at least one instance of R1 for each gamma carbon is an H, for example and without limitation, for each gamma carbon, one instance of R1 is an H and the other is an amino acid side chain, and each gamma carbon has the same amino acid side chain at R1. In another embodiment, R1s at each gamma carbon are the same.

In one embodiment, one or more instances of R are selected from the group consisting of JB1, JB2, JB3, JB4, JB5, JB6, JB7, JB8, JB9, JB9b, JB10, JB11, JB12, JB13, JB14, JB15, and JB16 and/or the group consisting of adenine, guanine, thymine, cytosine, uracil, hypoxanthine, xanthene, 7-methylguanine, 5, 6, dihydrouracil, 5-methylcytosine, and 5-hydroxymethylcytosine and/or the group consisting of a nucleobase of FIG. 4A. In one embodiment, the nucleobases R of both of the plurality of recognition modules are arranged in a sequence complementary to target sequences of the template nucleic acid so that each of the plurality of recognition modules bind to sequences of bases on the template nucleic acid and ligate to each other. In another embodiment, nucleobases R of both of the plurality of recognition modules are arranged in a sequence complementary to adjacent portions of a contiguous target sequence of nucleobases of the template nucleic acid so that each of the plurality of recognition modules bind adjacent to each other on the contiguous target sequence of nucleobases on the template nucleic acid. In yet another embodiment, the sequence of nucleobases R for each of the plurality of recognition modules is the same.

in which, X is S or O; n is an integer from 1 to 6, inclusive; m is an integer from 0 to 4, inclusive; R1s each independently are selected from the group consisting of H, an amino acid side chain, linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, —$CH_2$—(O$CH_2$—$CH_2$)$_q$O$P_1$, —$CH_2$—(O$CH_2$—$CH_2$)$_q$—NH$P_1$, —$CH_2$—(O$CH_2$—$CH_2$-O)$_q$-S$P_1$ and —$CH_2$—(S$CH_2$—$CH_2$)$_q$—S$P_1$, —$CH_2$—(O$CH_2$—$CH_2$)$_r$—OH, —$CH_2$—(O$CH_2$—$CH_2$)$_r$—$NH_2$, —$CH_2$—(O$CH_2$—$CH_2$)$_r$—NHC(NH)$_2$, or —$CH_2$—(O$CH_2$—$CH_2$)$_r$—S—S[$CH_2CH_2$]$_s$NHC(NH)$NH_2$, where $P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene and $(C_3-C_8)$cycloalkyl $(C_1-C_6)$alkylene; q is an integer from 0 to 50, inclusive; r and s are each independently integers from 1 to 50, inclusive; R2 is selected from the group consisting of H, linear or branched $(C_1-C_8)$alkyl, substituted or unsubstituted $(C_3-C_8)$ aryl, $(C_3-C_8)$aryl$(C_1-C_6)$alkylene, $(C_1-C_8)$ carboxylic, or In one embodiment, the template nucleic acid is DNA or RNA. In another, the template nucleic acid is a nucleic acid analog. To facilitate purification of the product, the template nucleic acid is attached to a substrate, such as a bead according to certain embodiments. In one embodiment, the template is attached to a substrate and the method comprises: contacting the plurality of recognition molecules with the template nucleic acid; exposing the recognition molecules bound to the template nucleic acid to a reducing agent, thereby causing the recognition molecules bound to the template nucleic acid to ligate together to produce an extended γPNA oligomer; and eluting the γPNA oligomer from the template nucleic acid. In one non-limiting example, the method is performed in a column retaining the substrate and template nucleic acid. In one embodiment, the recognition modules have the same sequence and are complementary to a tandemly-repeated nucleobase sequence in the target nucleic acid. In another, the recognition molecules correspond to or are complementary to sequences presented in Table A, for example the sequence of nucleobases R for the recognition modules is selected from the group consisting of, from 5' to 3': GAA, CGG, CCG, CAG, CTG, CCTG, CGG, CTG, ATTCT, CAG, and GGGGCC or a sequence complementary thereto.

In another embodiment, the recognition module has the structure of Formula 2:

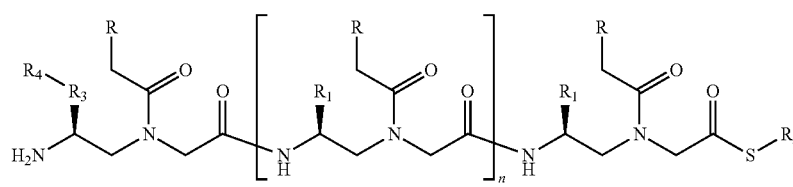

(2)

in which, R1s are each independently an amino acid side chain, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where r and s are each independently 1-50; R2 is selected from the group consisting of H, linear or branched (C$_1$-C$_8$)alkyl, substituted or unsubstituted (C$_3$-C$_8$)aryl, (C$_3$-C$_8$)aryl(C$_1$-C$_6$)alkylene, (C$_1$-C$_8$) carboxylic, or, or

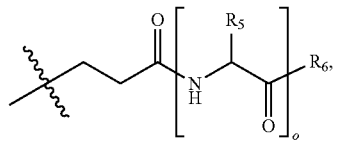

where o is 1-20, R5s are each independently an amino acid side chain and R6 is —OH or NH$_2$; and Rs are each independently nucleobases.

According to another embodiment, a composition is provided having the structure of Formula 1, in which, X is S or O; n is an integer from 1 to 6, inclusive; m is an integer from 0 to 4, inclusive; R1s each independently are selected from the group consisting of H, an amino acid side chain, linear or branched (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl(C$_1$-C$_6$)alkylene, —CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$-O)$_q$-SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene and (C$_3$-C$_8$)cycloalkyl (C$_1$-C$_6$)alkylene; q is an integer from 0 to 50, inclusive; r and s are each independently integers from 1 to 50, inclusive; R2 is selected from the group consisting of H, linear or branched (C$_1$-C$_8$)alkyl, substituted or unsubstituted (C$_3$-C$_8$)aryl, (C$_3$-C$_8$)aryl(C$_1$-C$_6$)alkylene, (C$_1$-C$_8$) carboxylic, or

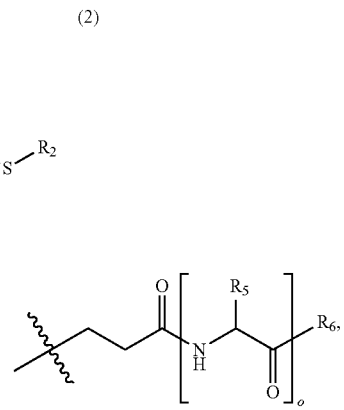

where o is 1-20, R5s are each independently an amino acid side chain and R6 is —OH or NH$_2$; R3 is (C$_1$-C$_{10}$) divalent hydrocarbon or (C$_1$-C$_{10}$) divalent hydrocarbon substituted with one or more N or O moieties, such as —O—, —OH, —C(O)—, —NH—, —NH$_2$, —C(O)NH—; R4 is —OH, —SH or a disulfide protecting group; and Rs each independently are nucleobases producing a sequence of nucleobases. In one embodiment, R4 has the structure —SH, —OH or —S—R7, where R7 is one or more amino acid residues, an amino acid side chain, linear, branched or hetero-substituted (C$_1$-C$_8$)alkyl, (C$_2$-C$_8$)alkenyl, (C$_2$-C$_8$)alkynyl, (C$_1$-C$_8$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl

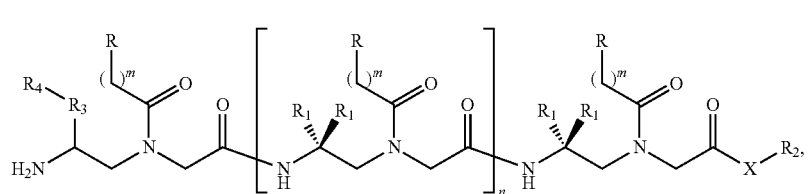

(1)

($C_1$-$C_6$)alkylene. In one embodiment, one or more instances of R are selected from the group consisting of JB 1, JB2, JB3, JB4, JB5, JB6, JB7, JB8, JB9, JB10, JB 11, JB12, JB13, JB14, JB15, JB16 and/or the group consisting of adenine, guanine, thymine, cytosine, uracil, hypoxanthene, xanthene, 7-methylguanine, 5, 6, dihydrouracil, 5-methyl-cytosine, and 5-hydroxymethylcytosine and/or the group consisting of a nucleobase of FIG. 4A. In a further embodiment, the sequence of nucleobases R are complementary to a target sequence of nucleobases in a template nucleic acid, for example, as above, the sequence of nucleobases R for the recognition module is selected from the group consisting of, from 5' to 3': GAA, CGG, CCG, CAG, CTG, CCTG, CGG, CTG, ATTCT, CAG, and GGGGCC or a sequence complementary thereto.

According to one embodiment, the composition has the structure of Formula 2:

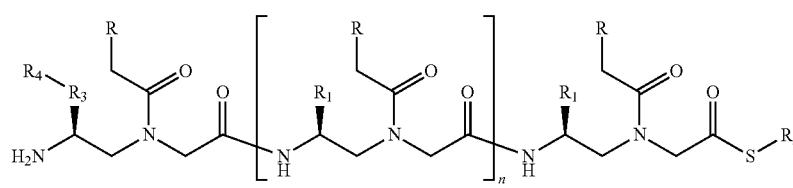

(2)

in which n is 1-6; R1s are each independently an amino acid side chain, —$CH_2$—(O$CH_2$—$CH_2$)$_r$—OH, —$CH_2$—(O$CH_2$—$CH_2$)$_r$—$NH_2$, —$CH_2$—(O$CH_2$—$CH_2$)$_r$—NHC(NH)$NH_2$, or —$CH_2$—(O$CH_2$—$CH_2$)$_r$—S—S[$CH_2CH_2$]$_s$NHC(NH)$NH_2$, where r and s are each independently 1-50; R2 is selected from the group consisting of H, linear or branched ($C_1$-$C_8$)alkyl, substituted or unsubstituted ($C_3$-$C_8$) aryl, ($C_3$-$C_8$)aryl($C_1$-$C_6$)alkylene, ($C_1$-$C_8$) carboxylic, or, or

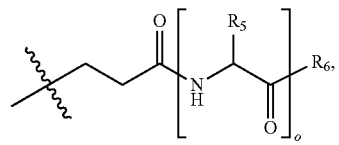

where o is 1-20, R5s are each independently an amino acid side chain and R6 is —OH or $NH_2$; and Rs are each independently nucleobases.

Also provided herein is a composition comprising the compound as described above and a transfection reagent, for example and without limitation a liposome.

In another embodiment, a kit is provided comprising a composition as described above in a vessel, and optionally the plurality of compositions as described above in a single vessel, or packaged separately. Vessels can be part of a multi-compartment (multi-vessel) cartridge for use in an automated system. The kit optionally comprises a transfection reagent.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

Figure 1:
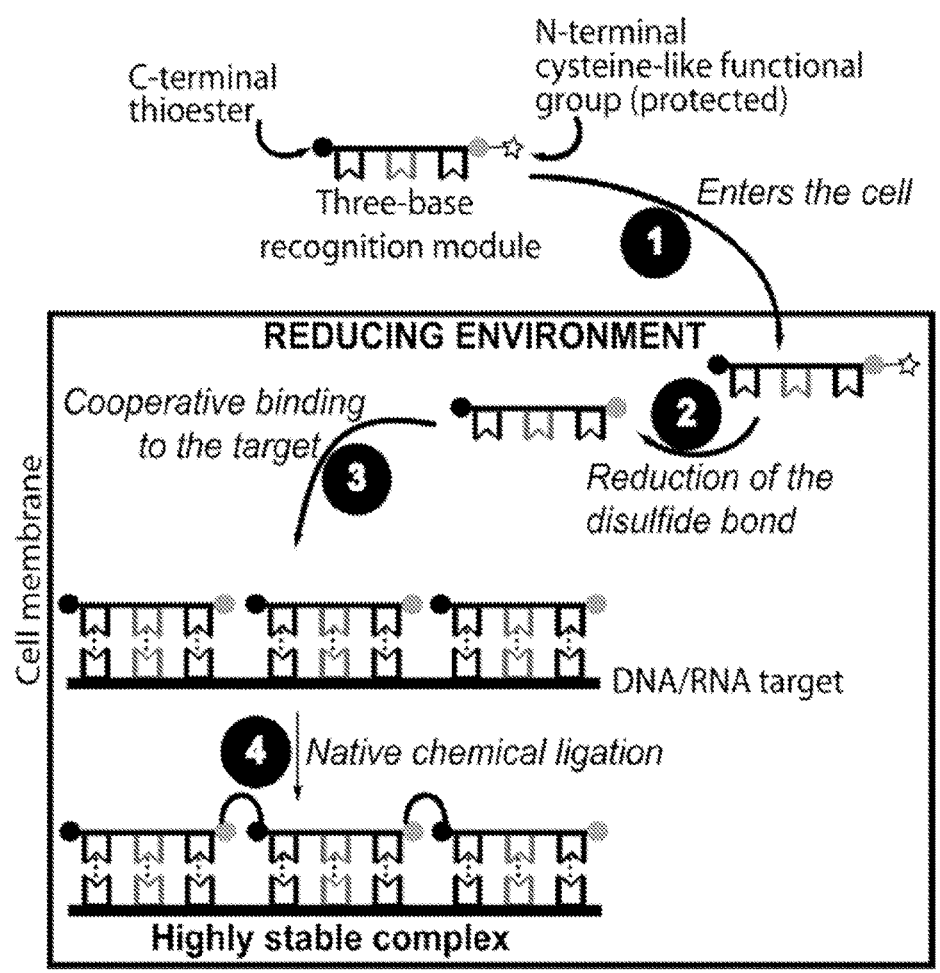
FIG. 1 illustrates a γPNA miniprobe containing a thioester at the C-terminus and cysteine (or cysteine-like residue) at the N-terminus entering a cell and initiating a template-directed 'native chemical ligation' reaction to form extended oligomers of varying lengths.

Provided herein are recognition modules—modified peptide nucleic acids—that assemble on a nucleic acid template and ligate together in a reducing environment, that is, in the presence of a reducing agent. FIG. 1 depicts the overall template-directed γPNA synthesis concept schematically using an exemplary three-base recognition module. A plurality of recognition modules bind by Watson-Crick or Watson-Crick-like cooperative base pairing to a template nucleic acid. In a cell a template nucleic acid is an RNA or DNA, though in vitro, a template nucleic acid can be and RNA or DNA, as well as modified nucleic acids or nucleic acid analogs. Thus a template nucleic acid is a composition comprising a nucleobases sequence and which can bind cooperatively to a DNA or RNA by Watson-Crick or Watson-Crick-like cooperative base pairing. Recognition modules in sufficient proximity, for example binding to adjacent sequences on a template, will ligate in a reducing environment, thus forming a longer oligomer or even a polymer.

Figure 2:
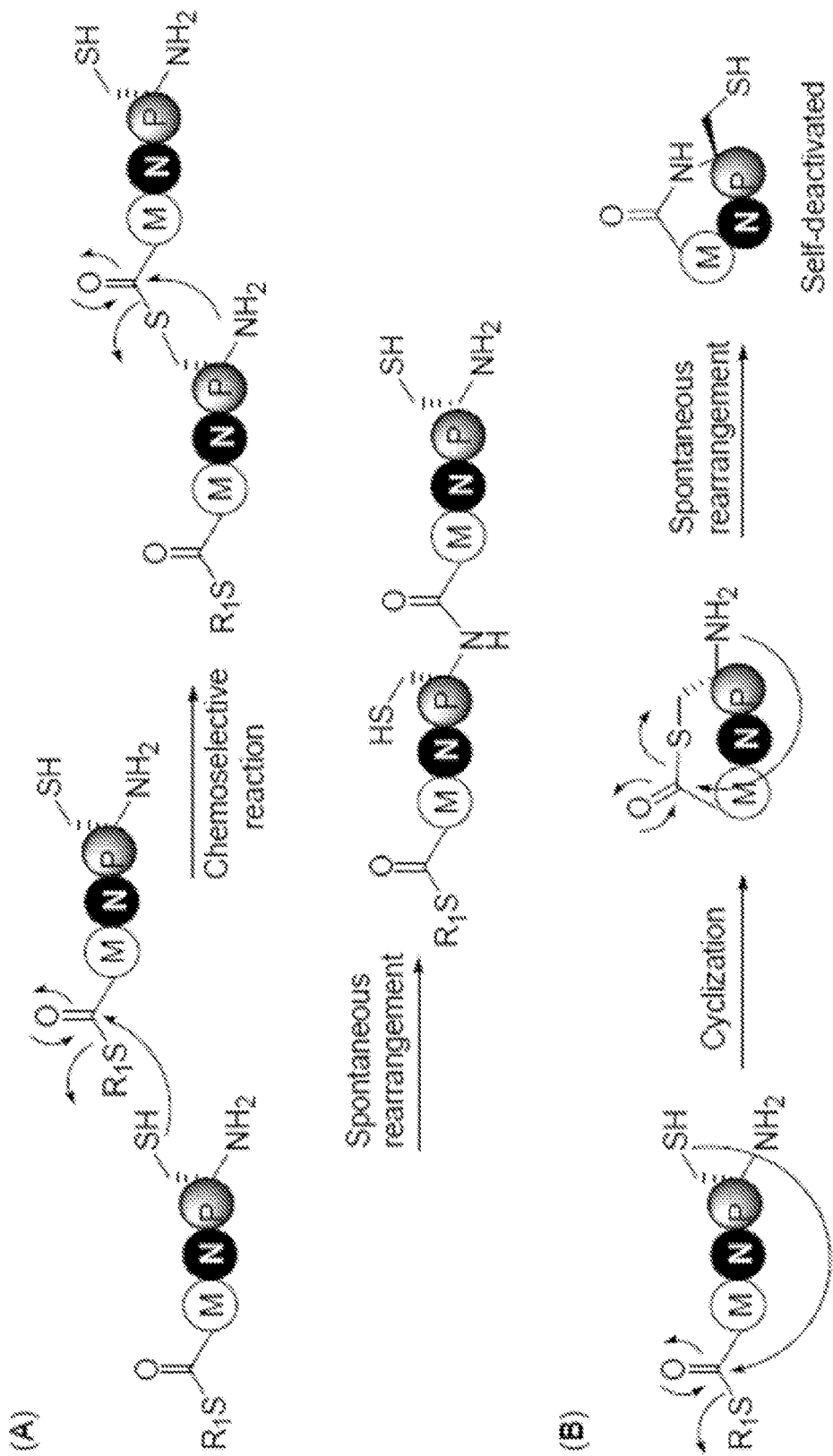
FIG. 2 illustrates a mechanism of intracellular (A) template-directed 'native chemical ligation' reaction, and (B) intramolecular cyclization (self-inactivation). In the presence of the target, path A predominates; in the absence of the target, path B predominates.

The recognition modules are unique in that they contain C-terminal thioester and N-terminal cysteine or cysteine-like (thiol) chemical functionalities. They are specifically designed to be chemically inert ex vivo until they enter the cytoplasm and nucleus of a cell, under which condition the protecting group is removed by intracellular glutathione through reduction of the disulfide bridge. One non-limiting embodiment is illustrated in FIG. 2. The recognition modules then recognize and bind their DNA or RNA target through cooperative Watson-Crick (or Watson-Crick-like, hydrogen bonding) base-pairing interactions, upon which the adjacent modules undergo spontaneous 'native chemical ligation' (NCL) reaction (Dawson, P. E.; et al., "Synthesis of proteins by native chemical ligation," Science 1994, 266, 776-779) to form extended, concatenated oligomers in a head-to-tail fashion, as shown in FIG. 2(A). The rate of intramolecular vs. intermolecular NCL reaction, or inactivation vs. concatenation, can be controlled by modulating the extent of base-stacking, length of oligomers, or rigidity of γPNA backbone (FIG. 2(B)). Importantly, in the presence of the target, the path of FIG. 2(A) predominates; in the absence of the target, the path of FIG. 2(B) predominates.

Figure 3:
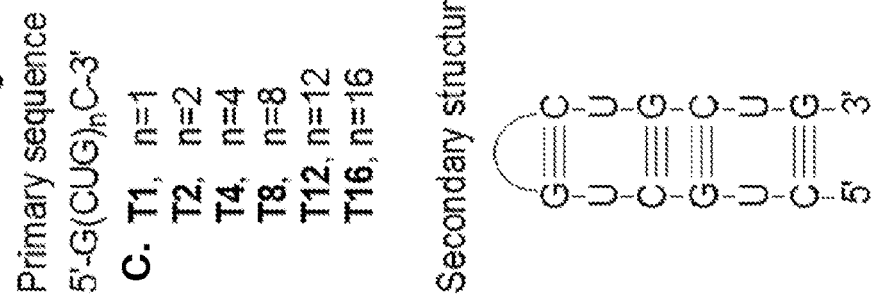
FIG. 3 (A,B) illustrates chemical composition of γPNA probes, and (C) sequence of RNA targets (SEQ ID NO: 1).
Figure 3:
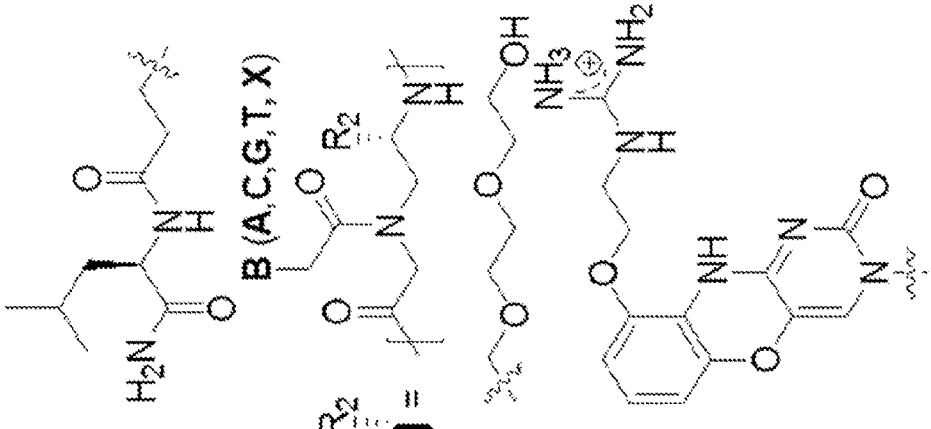
Figure 3:
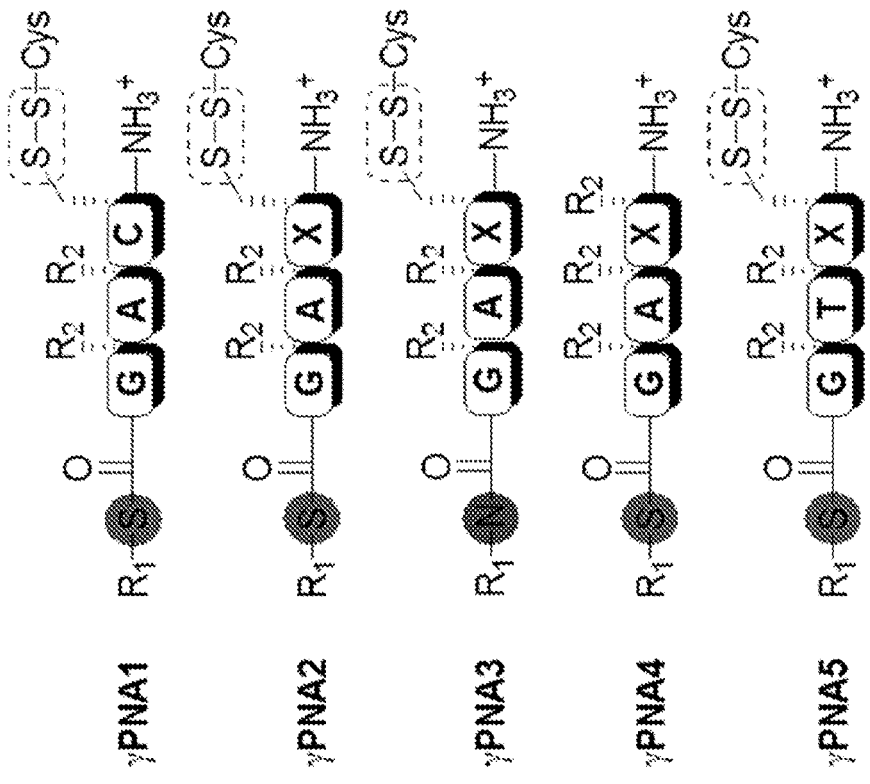

The methodology examples and γPNA probes described herein overcome the challenge of the scale and cost of oligonucleotide synthesis in the following respects. First, since the recognition modules are relatively small in size, 3 to 8 nucleotides (nt) in length and bordering the molecular weight of small-molecules and biomimetics for many of the intended therapeutic applications, they can be produced in large scale using convergent, solution-phase synthesis methods. Second, the large scale production would translate to cheaper production cost and greater accessibility to these materials for treatment. FIG. 3 shows the chemical compositions of some examples of γPNA probes (A and B) and examples of RNA targets.

The recognition modules (e.g., γPNAs) designed herein also overcome the cellular delivery limitations because of the reduced size of the recognition modules and flexibility in the chemical modifications. Because they are relatively small in size, they are taken-up more readily by cells and more permeable to the nuclear membrane. Further, because of their synthetic flexibility in that any chemical group can be incorporated in the backbone of γPNAs, these recognition modules can be easily modified with specific chemical functionalities to promote cellular uptake and systemic delivery (see, e.g., Sahu, B. et al. Synthesis of Conformationally Preorganized and Cell-Permeable Guanidine-Based γ-Peptide Nucleic Acids (γGPNAs), *J. Org. Chem.* 2009, 74, 1509-1516).

In the examples described, application of γPNAs also overcomes the nonspecific binding and cytotoxic effect issues by taking advantage of the weak interaction between the short recognition module (typically 3 to 8 nt in length) and the target. This weak "kissing" interaction permits the module to freely diffuse in the intracellular environment in search for its target. Its designated target, in this case, differs from the 'random', 'single-binding site' hit in that it contains repeated or adjacently-spaced sequence elements, which enable the module to assemble next to one another in a cooperative manner through adjacent base-stacking and commence a native chemical ligation reaction to form a series of extended oligomers of varying lengths. This has application both in vitro and in vivo as a template-directed oligonucleotide synthesis process.

The ability to control the rate of cyclization, or self-inactivation, is essential to the development of 'fail-safe' drugs for treatment of genetic and infectious diseases. The 'fail-safe' features emanate from the fact that if the repeated targets are not present in cells, the drugs will inactivate themselves through intramolecular cyclization. Another advantage of the present invention over the "small molecule drug" approach is in the treatment of cancer and in combating bacterial, viral, and parasitic infections, where the targets are rapidly evolving due to the rapid rate of mutations. There are a number of conserved and repeated elements within the genomes and transcriptomes of the tumorigenic clones and of the bacterial, viral, and parasitic pathogens that could potentially be targeted with this method and approach. The chance for these tumor cells or pathogens to evade these recognition modules described herein and become resistant is unlikely, as compared to the 'small molecule-protein recognition' approach because the mutation would have to occur at every repeat element within the DNA/RNA template. Even if this were to occur, although extremely unlikely in the lifespan of an organism, one can modify the sequence of the recognition module to recognize that of the emerging mutant—which is a difficult task to accomplish with 'small molecule drugs'. This would require redesigning and reengineering a new set of molecules, an endeavor that would take ~10-15 years to accomplish at the cost of billions of dollars.

Examples of applications for this γPNA template-directed method and approach can be used in the treatment of genetic diseases, in particular those listed in Table A.

TABLE A

Genetic diseases associated with unstable repeats

| Disease | Repeat Unit | Gene Name | Normal Repeat Length | Pathogenic Repeat Length |
|---|---|---|---|---|
| FRDA | (GAA)n | FRDA (frataxin) | 6-32 | 200-1,700 |
| FRAXA | (CGG)n | FMR1 (FMRP) | 6-60 | >200 |
| FRAXE | (CCG)n | FMR2 (FMR2) | 4-39 | 200-900 |
| SCA1 | (CAG)n | SCA1 (ataxin 1) | 6-39 | 40-82 |
| SCA2 | (CAG)n | SCA2 (ataxin 2) | 15-24 | 32-200 |
| SCA3 (MJD) | (CAG)n | SCA3 (ataxin 3) | 13-36 | 61-84 |
| SCA6 | (CAG)n | CACNA1A | 4-20 | 20-29 |
| SCA7 | (CAG)n | SCA7 (ataxin 7) | 4-35 | 37-306 |
| SCA17 | (CAG)n | SCA17 (TBP) | 25-42 | 47-63 |
| DRPLA | (CAG)n | DRPLA (atrophin 1) | 7-34 | 49-88 |
| SBMA | (CAG)n | AR (androgen receptor) | 9-36 | 38-62 |
| HD | (CAG)n | HD (huntingtin) | 11-34 | 40-121 |
| MD1 | (CTG)n | DMPK (DMPK) | 5-37 | 50-1,000 |
| MD2 | (CCTG)n | ZNF9 (ZNF9) | 10-26 | 75-11,000 |
| FXTAS | (CGG)n | FMR1 (FMRP) | 6-60 | 60-200 |
| SCA8 | (CTG)n | SCA8 | 16-34 | >74 |
| SCA10 | (ATTCT)n | Unknown | 10-20 | 500-4,500 |
| SCA12 | (CAG)n | PPP2R2B | 7-45 | 55-78 |
| HDL2 | (CTG)n | JPH3 | 7-28 | 66-78 |
| ALS | (GGGGCC)n | C9ORF72 | 20-50 | >100 |

Based on Table A, recognition modules that would target gene products described above include the sequences: GAA, CGG, CCG, CAG, CTG, CCTG, CGG, CTG, ATTCT, CAG, and GGGGCC or a sequence complementary thereto, e.g., TTC, CCG, CGG, CTG, CAGG, CCG, CAG, AGAAT or GGCCCC in a 5' to 3' direction (N-terminal to C-terminal (thioester), in the context of the described γPNA recognition modules).

Other potential applications of this invention are in the treatment of cancer (telomere), bacterial infection (resistant strains, targeting the repeated and conserved elements unique to the pathogenic strains), hepatitis C (affecting 3% of the world population for which there are no effective treatment by targeting the repeated elements within the viral RNA genome), malaria (targeting microsatellites that have been shown to be essential in the replication and life cycle of the plasmodium), and AIDS (this is a rapidly moving target for which the new mutant sequence can be chased after by dialing-in the corresponding nucleobase sequence in the recognition modules).

The recognition modules described herein combine the features of small molecules, for example, low molecular weight, ease of large-scale production, low production cost, cell permeability, and desired pharmacokinetics, with the sequence-specific recognition of oligonucleotides via Watson-Crick base-pairings. The DNA/RNA template-directed synthesis or 'native chemical ligation' by γPNA oligonucleotide probes has been demonstrated and described in accordance with several examples, which are intended to be illustrative in all aspects rather than restrictive. Thus, the present invention is capable of many variations in detailed implementation, which may be derived from the description contained herein by a person of ordinary skill in the art. As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

By "expression" or "gene expression," it is meant the overall flow of information from a gene (without limitation, a functional genetic unit for producing a gene product, such as RNA or a protein in a cell, or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

As used herein, the term "knockdown" means that expression of one or more genes in an organism is reduced, typically significantly, with respect to a functional gene, such as to a therapeutically-effective degree. Gene knockdown also includes complete gene silencing. As used herein, "gene silencing" means that expression of a gene is essentially completely prevented. Knockdown and gene silencing may occur either at the transcriptional stage or the translational stage. Use of the described recognition modules, e.g., γPNA precursors, to target an RNA in a cell, such as an mRNA, will modify gene expression, by knocking down or silencing a gene or genes at the translational stage.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, threose nucleic acids and combinations thereof including, optionally ribonucleotide or deoxyribonucleotide residue(s). Herein, "nucleic acid" and "oligonucleotide", which is a short, single-stranded structure made of up nucleotides, are used interchangeably. An oligonucleotide may be referred to by the length (i.e. number of nucleotides) of the strand, through the nomenclature "-mer". For example, an oligonucleotide of 22 nucleotides would be referred to as a 22-mer.

A "peptide nucleic acid" refers to a DNA or RNA mimic in which the sugar phosphodiester backbone of the DNA or RNA is replaced by a N-(2-aminoethyl)glycine unit. A gamma PNA (γPNA) is an oligomer or polymer of gamma-modified N-(2-aminoethyl)glycine monomers of the following structure:

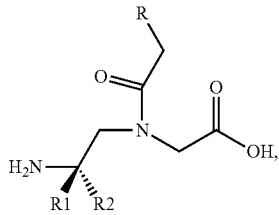

is referred to herein as a γPNA "residue", with each residue having the same or different R group as its base (nucleobase), such as adenine, guanine, cytosine, thymine and uracil bases, or other bases, such as the monovalent and divalent bases described herein, such that the order of bases on the PNA is its "sequence", as with DNA or RNA. A sequence of nucleobases in a nucleic acid or a nucleic acid analog oligomer or polymer, such as a PNA or γPNA oligomer or polymers, binds to a complementary sequence of adenine, guanine, cytosine, thymine and/or uracil residues in a nucleic acid or nucleic acid analog strand by nucleobase pairing, essentially as with double-stranded DNA or RNA.

According to one embodiment of the present invention, a PNA, and in one particular embodiment, a γPNA is provided. Unlike traditional antisense, gene silencing and antigen approaches, which utilize relatively long oligonucleotides, typically in the order of 10-30 nucleotides in length, the compositions and methods described herein utilize relatively short, chiral γ-peptide nucleic acid (γPNA) oligomers ("recognition modules"), in the order of 2-10 or 3-8 PNA monomer residues in length, that are end-modified with a thiol and an amine on one end and a thioester on the other. When aligned on a template nucleic acid or nucleic acid analog tandemly or in another manner such that the thiol on a first recognition module molecule is in proximity to the thioester on a second recognition module, the two molecules will undergo "native chemical ligation," resulting in a ligated oligomer with a peptide bond between the first and second recognition module. A non-limiting example of the γPNA compositions is provided in Formula 1:

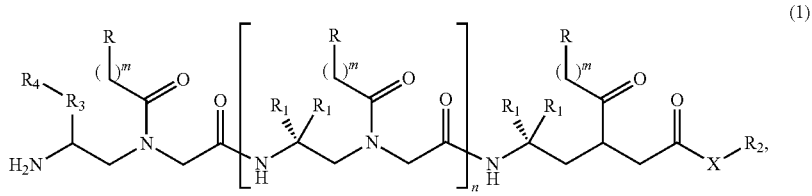

(1)

where at least one of R1 or R2 attached to the gamma carbon is not a hydrogen, such that the gamma carbon is a chiral center. When R1 and R2 are hydrogen (N-(2-aminoethyl)-glycine backbone), there is no such chirality about the gamma carbon. An incorporated γPNA monomer,

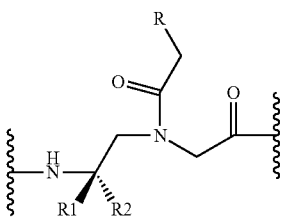

in which, X is S or O; n is an integer from 1 to 6, inclusive; m is an integer from 0 to 4, inclusive; R1s each independently are selected from the group consisting of H, an amino acid side chain, linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, $-CH_2-(OCH_2-CH_2)_q OP_1$, $-CH_2-(OCH_2-CH_2)_q-NHP_1$, $-CH_2-(OCH_2-CH_2-O)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S[CH_2CH_2]_sNHC(NH)NH_2$, where $P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene and $(C_3-C_8)$cycloalkyl $(C_1-C_6)$alkylene; q is an integer from 0 to 50, inclusive; r and s are each independently integers from 1 to 50, inclusive; R2 is selected from the group consisting of H, linear or branched $(C_1-C_8)$alkyl, substituted or unsubstituted $(C_3-C_8)$ aryl, $(C_3-C_8)$aryl$(C_1-C_6)$alkylene, $(C_1-C_8)$ carboxylic, or

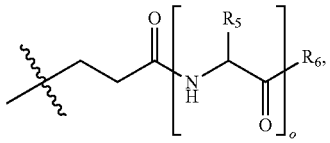

where o is 1-20, R5s are each independently an amino acid side chain and R6 is —OH or $NH_2$; R3 is $(C_1-C_{10})$ divalent hydrocarbon or $(C_1-C_{10})$ divalent hydrocarbon substituted with one or more N or O moieties, such as —O—, —OH, —C(O)—, —NH—, —$NH_2$, —C(O)NH—; R4 is —OH, —SH or a disulfide protecting group (a removable group attached to the recognition module by a disulfide bond, and not interfering substantially with the native-chemical ligation or circularization of the recognition module when reduced, converting the disulfide to an —SH on the recognition module); and Rs each independently are nucleobases producing a sequence of nucleobases. In non-limiting embodiments, R4 has the structure —SH, —OH, or —S—R7, where R7 is one or more amino acid residues, an amino acid side chain, linear, branched or hetero-substituted (that is, one or more carbons are substituted with or replaced by one or more of S, O, N or P) $(C_1-C_8)$alkyl, $(C_2-C_8)$ alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene. In certain non-limiting embodiments, nucleobase(s) are chosen from those depicted in FIGS. 4A (monovalent nucleobases) and 4B (divalent nucleobases). For JB7, JB8, JB15 and JB16, X is CH or N. In one embodiment, all instances of X are CH. For divalent nucleobases JB1-JB16, shown in FIG. 4B, Table B shows their specificity. Of note, JB1-JB4 bind complementary bases (C-G, G-C, A-T and T-A), while JB5-JB16 bind mismatches, and thus can be used to bind two strands of matched and/or mismatched bases.

TABLE B

| Divalent Nucleobases | |
|---|---|
| Nucleobase | Bases represented |
| JB1 | T/D* |
| JB2 | D/T |
| JB3 | G/C |
| JB4 | C/G |
| JB5 | C/C |
| JB6 | U/U |
| JB7 | G/G |
| JB8 | D/D |
| JB9/JB9b | A/C |

TABLE B-continued

| Divalent Nucleobases | |
|---|---|
| Nucleobase | Bases represented |
| JB10 | C/A |
| JB11 | U/G |
| JB12 | G/U |
| JB13 | C/U |
| JB14 | U/C |
| JB15 | G/D |
| JB16 | D/G |

*diaminopurine, an adenine analog.

Exemplary γPNA structures that are not end-modified in the manner described herein, but which may be, are disclosed in International Patent Publication No. WO 2012/138955.

In another embodiment, the recognition module has the structure of Formula 2:

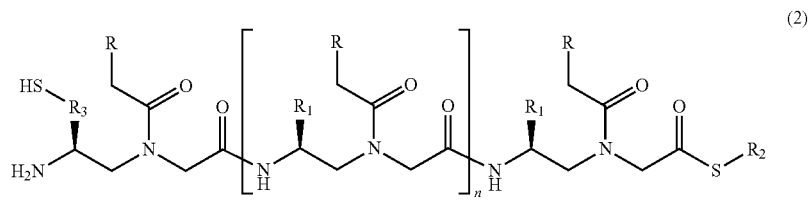

(2)

in which n is 1-6; R1s are each independently an amino acid side chain, —$CH_2$—$(OCH_2$—$CH_2)_r$—OH, —$CH_2$—$(OCH_2$—$CH_2)_r$—$NH_2$, —$CH_2$—$(OCH_2$—$CH_2)_r$—NHC(NH)$NH_2$, or —$CH_2$—$(OCH_2$—$CH_2)_r$—S—$S[CH_2CH_2]_s$ NHC(NH)$NH_2$, where r and s are each independently 1-50; R2 is selected from the group consisting of H, linear or branched $(C_1-C_8)$alkyl, substituted or unsubstituted $(C_3-C_8)$ aryl, $(C_3-C_8)$aryl$(C_1-C_6)$alkylene, $(C_1-C_8)$ carboxylic, or, or

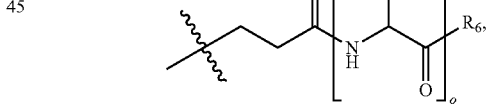

where o is 1-20, R5s are each independently an amino acid side chain and R6 is —OH or $NH_2$; and Rs are each independently nucleobases. In one embodiment all instances of R1 are the same. One non-limiting embodiment of R2 is 3-mercaptopropionic acid (3-MPA,

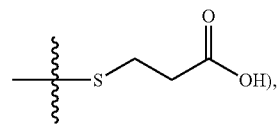

optionally including one or more of any combination of amino acids (e.g.,

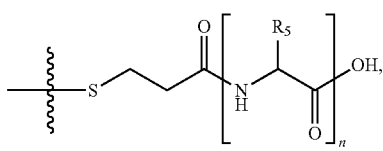

where n is one or more, e.g., 1 to 20, 1 to 10 or 1 to 5 and each instance of R, independently is an amino acid side chain).

R groups of the recognition modules described herein are arranged in a sequence to be complementary to a sequence of nucleobases in template nucleic acid(s) so that the compositions will bind to the sequence of nucleobases in the template nucleic acid(s). A "template nucleic acid" includes any nucleic acid or nucleic acid analog, and does not necessarily refer to a "nucleic acid" per se. In the methods described herein, the template nucleic acid serves as template to which two or more recognition modules bind specifically and undergo native chemical ligation. When the template is within a cell, it likely will be a nucleic acid, such as DNA or RNA, such as an mRNA to silence. If the recognition modules are assembled in vitro, the template can be a nucleic acid or any analog thereof that permits specific hybridization to the recognition modules described herein.

Figure 5:
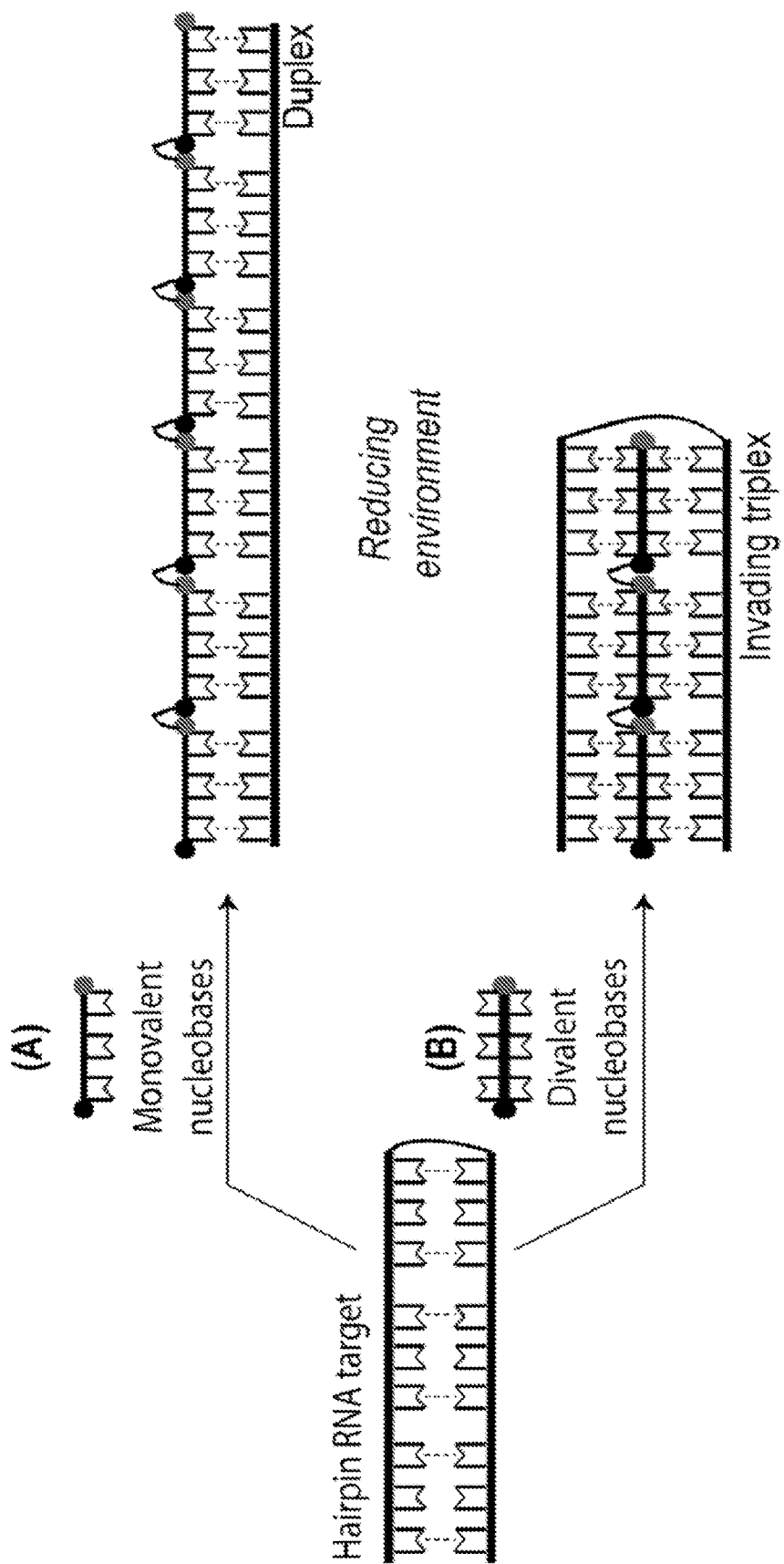
FIGS. 5A and 5B depict schematically binding of recognition modules having monovalent nucleobases (FIG. 5A) or divalent nucleobases (FIG. 5B).

The template nucleic acid comprises one or more target sequences of bases to which the recognition modules described herein bind specifically. The target sequences do not necessarily have to be contiguous (in unbroken sequence), but can include gaps, so long as the compositions described herein can both bind specifically to the sequences and are in sufficient proximity that they can undergo native chemical ligation. In the context of this disclosure and the recognition modules described herein, the term "ligate" refers to the native chemical ligation reaction by which two recognition modules of the composition described herein, irrespective of whether the sequences of the oligomers are the same or different, covalently join to form a longer oligomer or even a polymer, for example and without limitation by the mechanism shown in FIG. 2(A). According to one embodiment, two of the recognition modules described herein bind to different portions of the template nucleic acid adjacent to each-other on the template strand, thereby binding a contiguous sequence of bases in the template nucleic acid without gaps so that, when ligated, the resulting oligomer binds a contiguous sequence of bases of the template nucleic acid, as shown in FIG. 5(A). Where the composition comprises bases that are divalent, meaning they bind to both opposite strands of double-stranded sequence, such as in a hairpin structure (see, FIG. 5B) or other matched or mismatched secondary structure, or in matched (no mismatches) duplexed nucleic acid. Note in FIGS. 5A and 5B, the joined oligomers are depicted as having a junction (curved), yet that is done to depict the ligation sites, and in reality is simply a peptide (amide) bond as depicted in FIG. 2A, and base-paired nucleobases are depicted by dashed lines.

Unless otherwise indicated, the recognition modules described herein are not described with respect to any particular sequence of bases. The present disclosure is directed to methods and compositions for joining the γPNA backbone, and is independent of the identity and sequence of bases attached thereto. Based on the abundance of published work with nucleic acids, nucleic acid analogs and PNA (e.g., γPNA), it is expected that any nucleobase sequence attached to the backbone of the described γPNA oligomers would hybridize in an expected, specific manner with a complementary nucleobases sequence of a target nucleic acid or nucleic acid analog by Watson-Crick or Watson-Crick-like hydrogen bonding. One of ordinary skill would understand that the compositions and methods described herein are sequence-independent and describe a novel, generalized method, and related compositions, for template-directed assembly of longer γPNA sequences from shorter γPNA (precursor) sequences.

Figures 1, 4A:
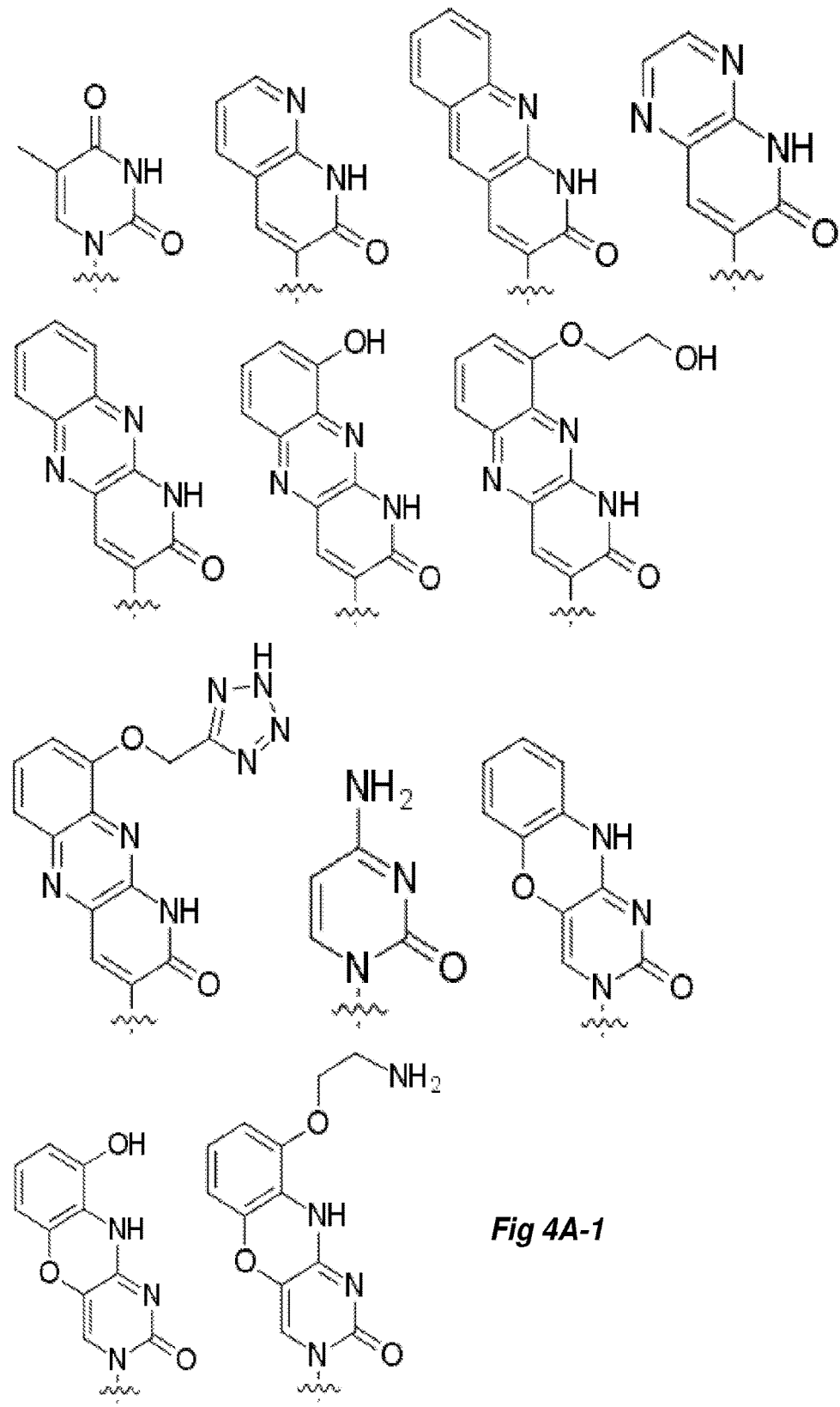
FIGS. 4A and 4B show non-limiting examples of monovalent nucleobases and divalent nucleobases, respectively.
Figures 2, 4A:
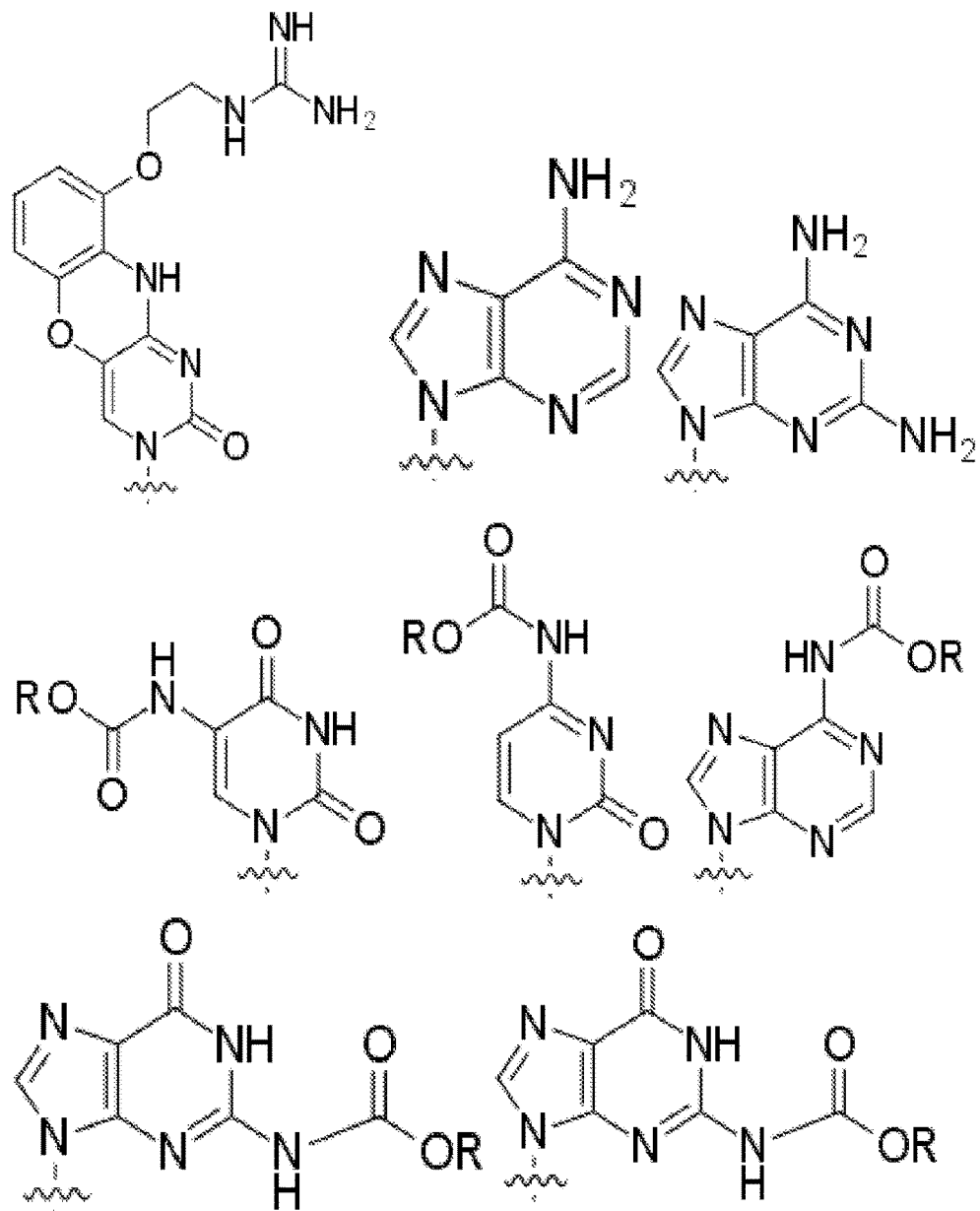
Figures 1, 4B:
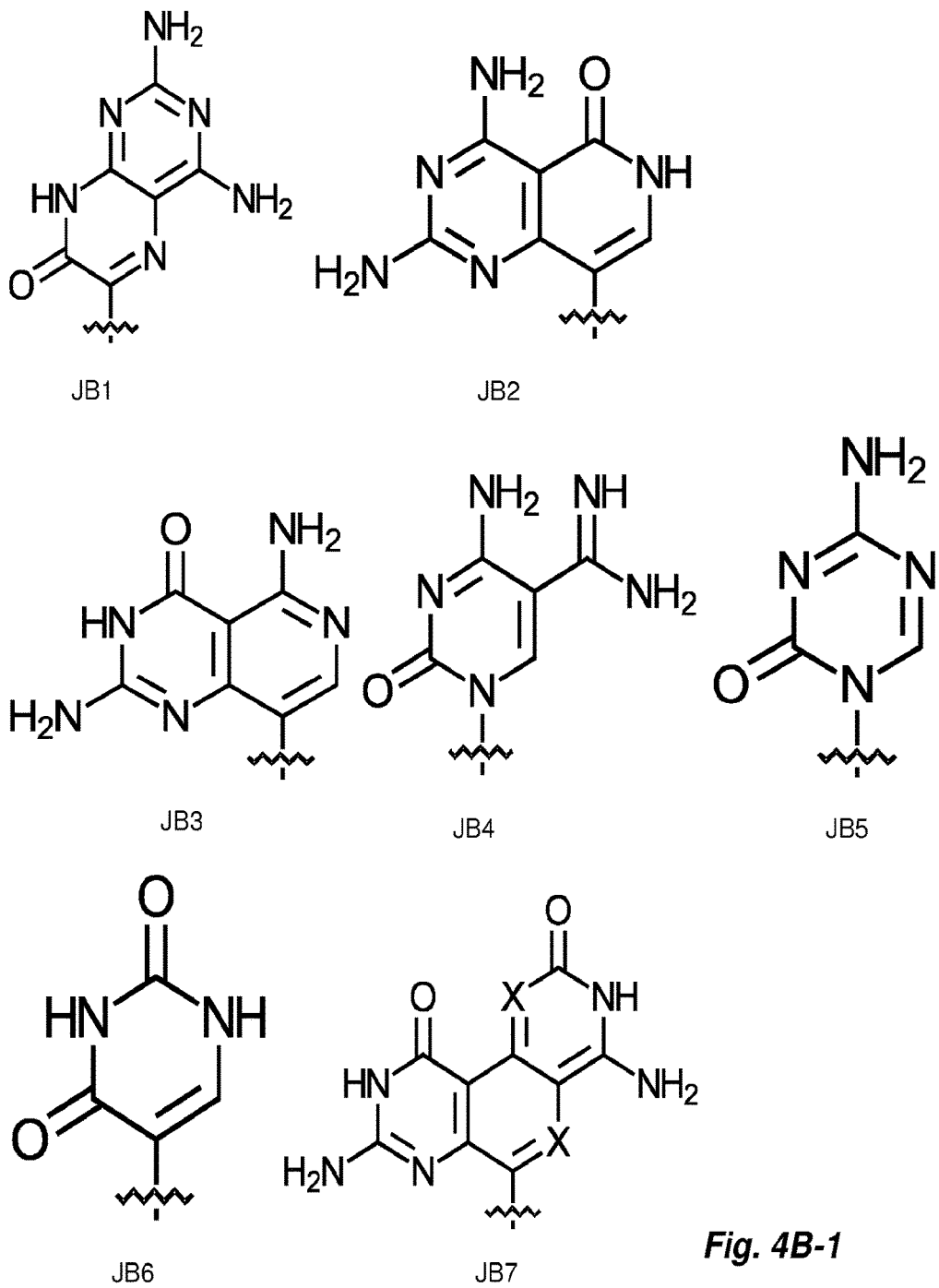
Figures 2, 4B:
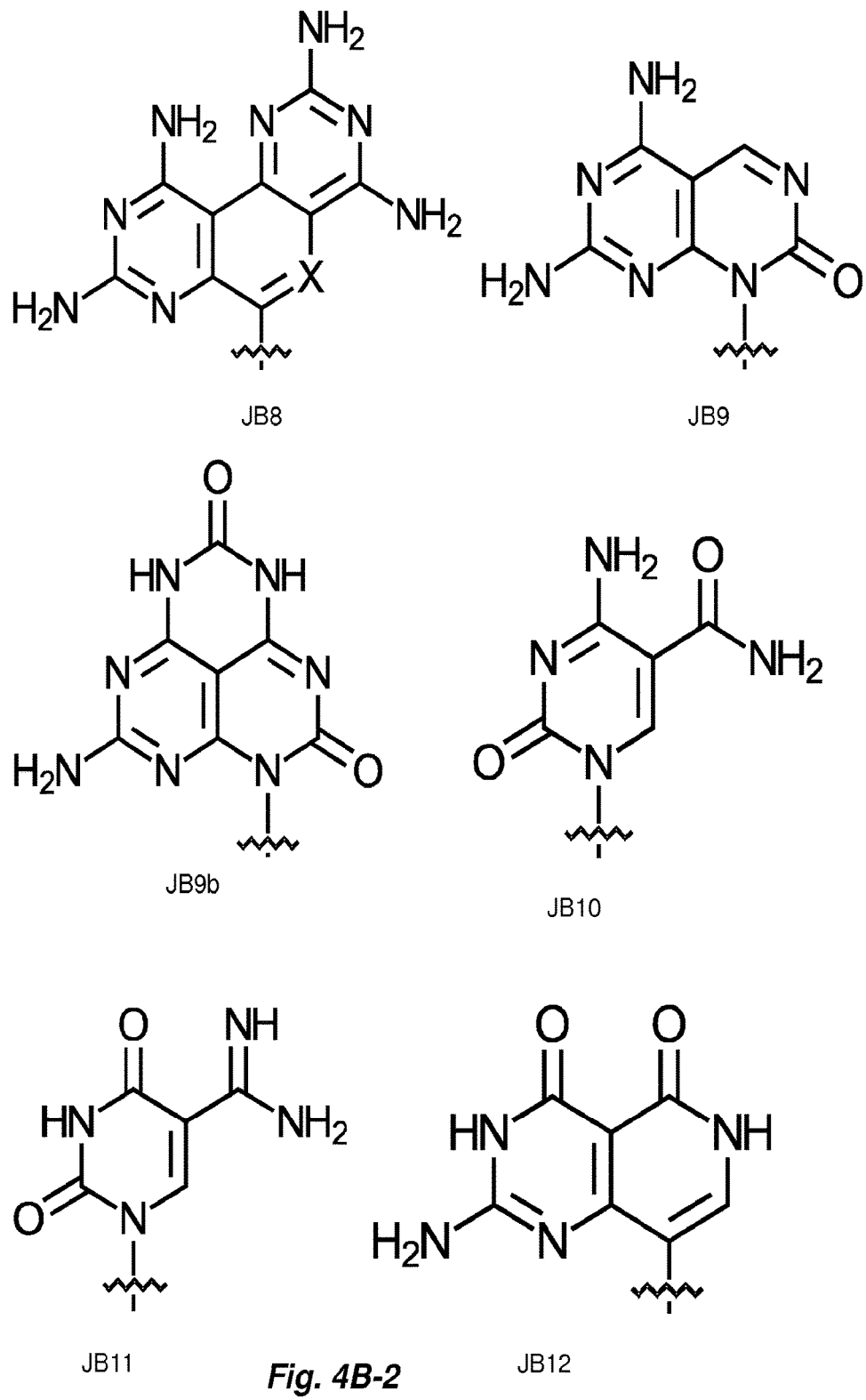

Nucleobases are recognition moieties that bind specifically to one or more of adenine, guanine, thymine, cytosine, and uracil, e.g., by Watson-Crick or Watson-Crick-like base pairing by hydrogen bonding. A "nucleobase" includes primary nucleobases: adenine, guanine, thymine, cytosine, and uracil, as well as modified purine and pyrimidine bases, such as, without limitation, hypoxanthine, xanthene, 7-methylguanine, 5, 6, dihydrouracil, 5-methylcytosine, and 5-hydroxymethylcytosine. FIGS. 4A and 4B also depict non-limiting examples of nucleobases, including monovalent nucleobases (e.g., adenine, cytosine, guanine, thymine or uracil, which bind to one strand of nucleic acid or nucleic acid analogs), and divalent nucleobases (e.g., JB1-JB16 described herein) which bind complementary nucleobases on two strands of DNA simultaneously, and "clamp" nucleobases, such as a "G-clamp," which binds complementary nucleobases with enhanced strength. Additional purine, purine-like, pyrimidine and pyrimidine-like nucleobases are known in the art, for example as disclosed in U.S. Pat. Nos. 8,053,212, 8,389,703, and 8,653,254.

Nucleobases of the recognition modules described herein are arranged in a sequence complementary to target sequences of the template nucleic acid so that two or more recognition modules as described herein bind by Watson-Crick, or Watson-Crick-like base pairing (e.g., hydrogen bonding) to sequences of bases on the template nucleic acid and ligate to each other. Non-limiting examples of the combinations of recognition modules that may be assembled according to the methods described herein are a two recognition modules in which a first recognition module has a nucleobases sequence complementary to a first sequence of a template nucleic acid or nucleic acid analog, and a second recognition module has a nucleobases sequence complementary to a second sequence on the template immediately adjacent to the first sequence on the template, such that the two precursors bind a contiguous series of bases on the template. For example and without limitation:

```
Template:              5' A-T-A-T-C-C-G-G-A 3'

Recognition modules:   3'    A-T-A G-G-C    5'

Ligated product:       3'    A-T-A-G-G-C    5'.
```

Two or more different recognition modules can be assembled in that manner, with each binding adjacent short sequences in a longer, contiguous sequence of the template nucleic acid, and ligating to adjacent recognition modules. In another non-limiting example, the recognition module has a single sequence of nucleobases complementary to a repeated sequence on the template so that two or more identical recognition modules bind tandemly to a contiguous sequence of repeats on the template:

```
Template:              5' A-T-A-A-T-A-A-T-T 3'

Recognition modules:   3' T-A-T T-A-T T-A-T 5'

Ligated product:       3' T-A-T-T-A-T-T-A-T 5'.
```

As indicated above, based on Table A, recognition modules that would target gene products described above include TTC, CCG, CGG, CTG, CAGG, CCG, CAG, AGAAT or GGCCCC.

Figure 6:
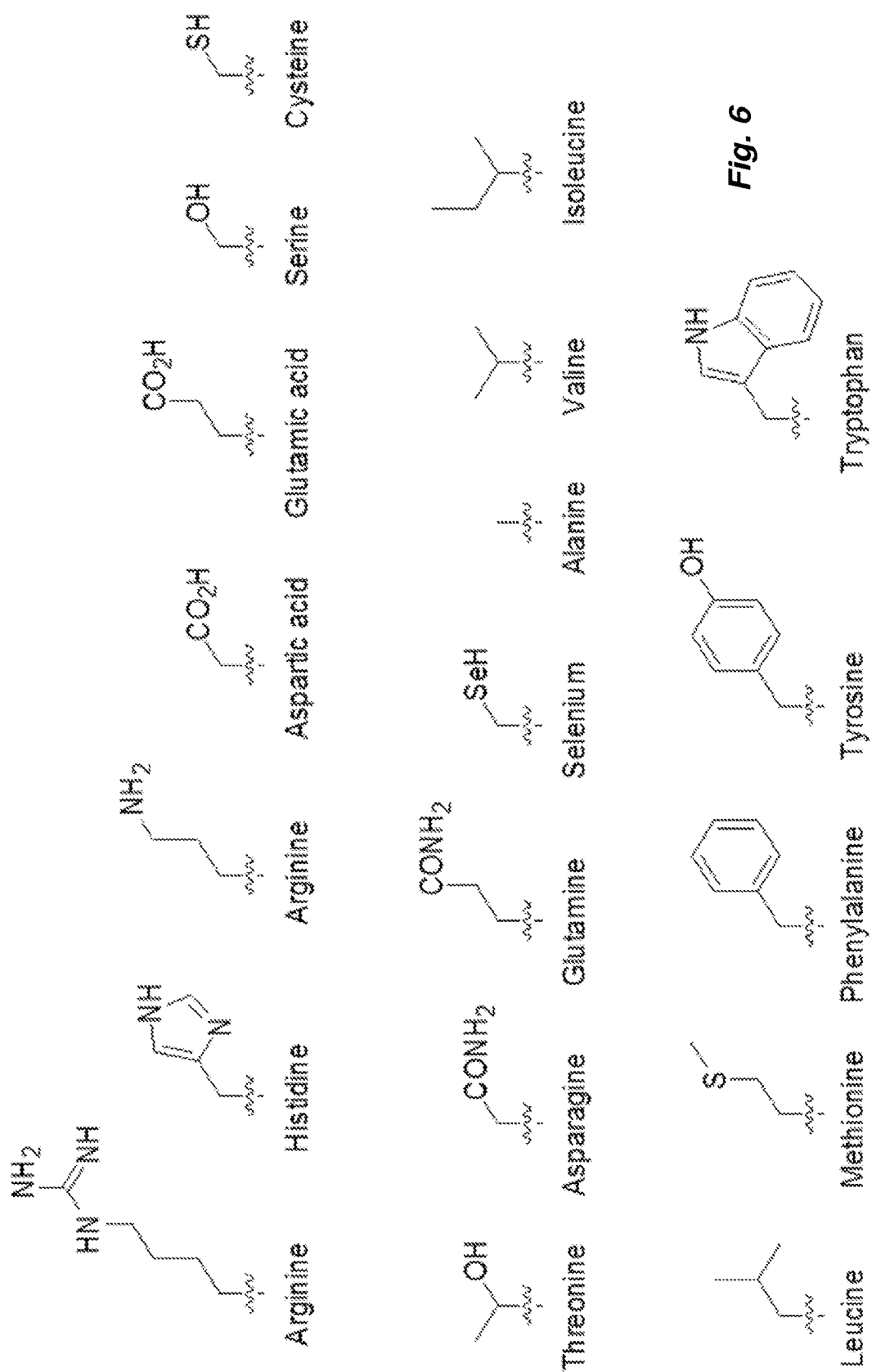
FIG. 6 provides structures of certain amino acid side chains.

An "amino acid side chain" is a side chain for an amino acid. Amino acids have the structure:

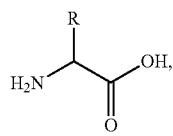

where R is the amino acid side chain. Non-limiting examples of amino acid side chains are shown in FIG. 6. Glycine is not represented because in the embodiment R1s are both H, which would not yield a γPNA.

Figure 7:
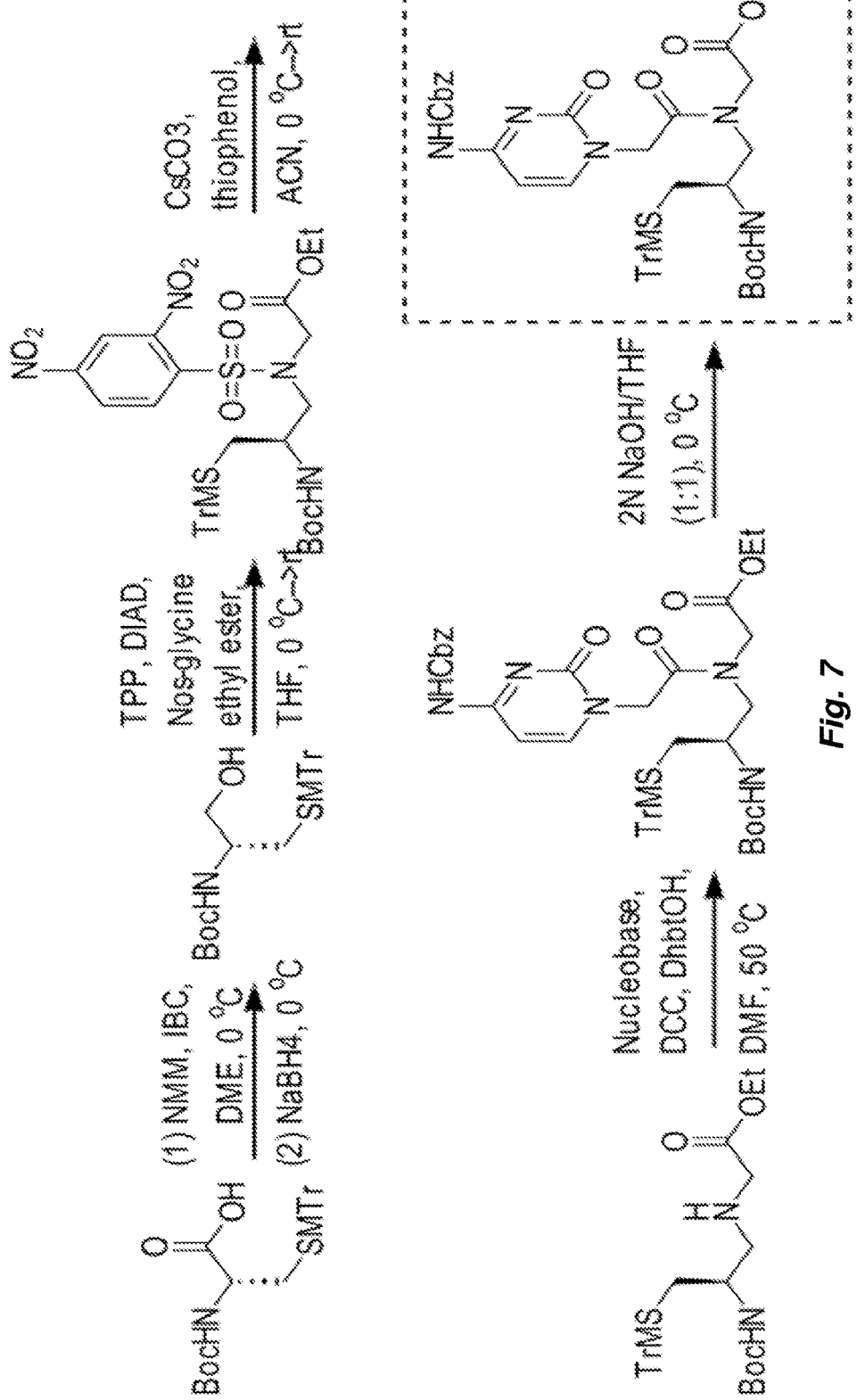
FIG. 7 provides an exemplary method of preparing method of making N-terminal cysteine γPNA monomers.
Figure 8:
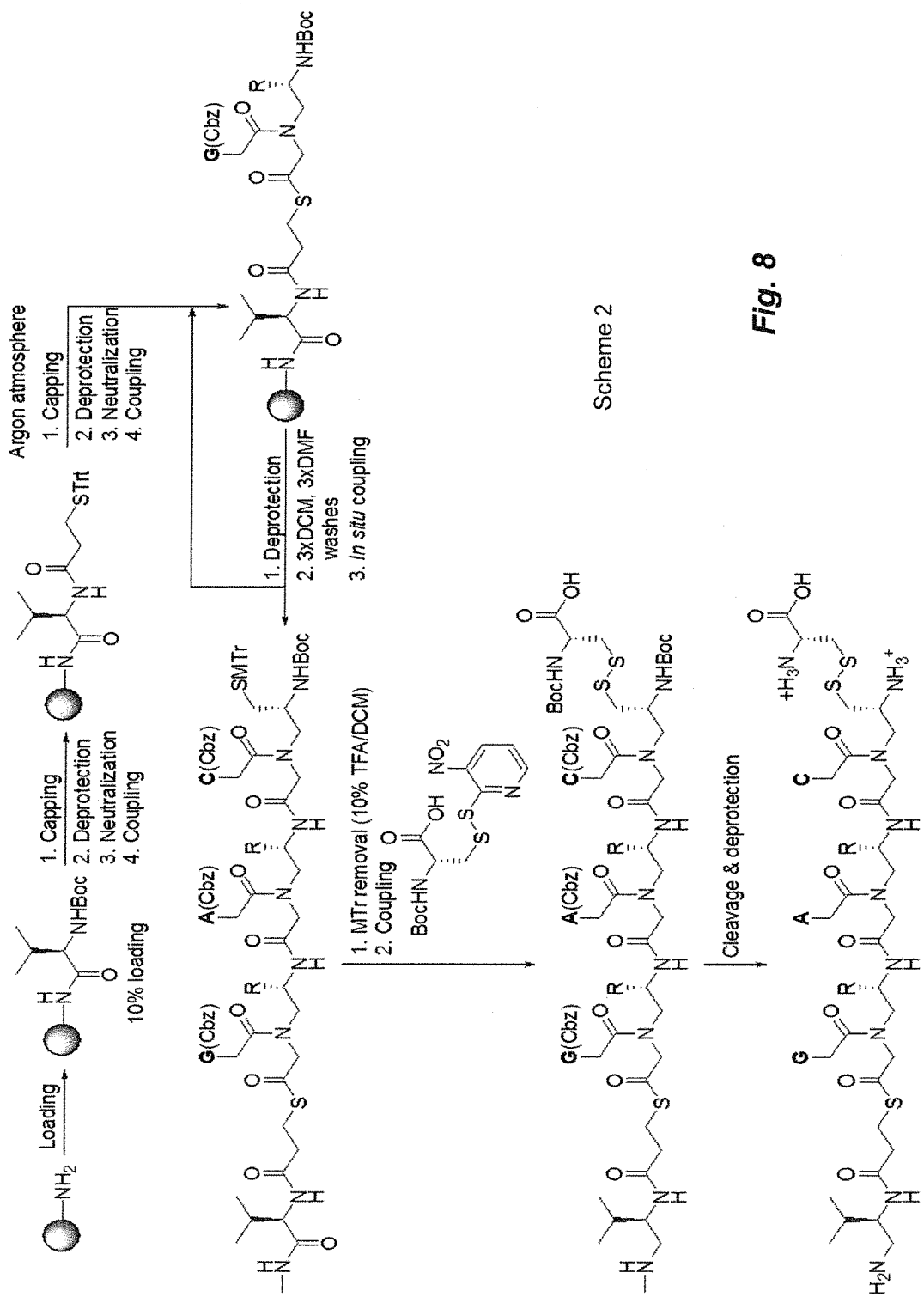
FIG. 8 provides an exemplary method of preparation of oligomers having the C-terminal thioester and N-terminal disulfide protective group.

Scheme 1, as provided in FIG. 7, is an exemplary method of making N-terminal cysteine γPNA monomers. Scheme 2, shown in FIG. 8, shows preparation of oligomers having the C-terminal thioester and N-terminal disulfide protective group.

The following are exemplary definitions of various structural elements described herein. As used herein, "alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—CH$_2$—CH$_2$—). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne" or "alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof. The term "ether" or "oxygen ether" refers to ($C_1$-$C_{10}$)alkyl group wherein one or more of the alkyl group's carbon atoms is replaced with an —O— group. The term ether includes —CH$_2$—(OCH$_2$—CH$_2$)$_q$OP$_1$ compounds where P$_1$ is a protecting group, —H, or a ($C_1$-$C_{10}$)alkyl. Exemplary ethers include polyethylene glycol, diethylether, methylhexyl ether and the like.

The term "thioether" refers to ($C_1$-$C_{10}$)alkyl group wherein one or more of the alkyl group's carbon atoms is replaced with an —S— group. The term thioether includes —CH$_2$—(SCH$_2$—CH$_2$)$_q$—SP$_1$ compounds where P$_1$ is a protecting group, —H, or a ($C_1$-$C_{10}$)alkyl. Exemplary thioethers include dimethylthioether, ethylmethyl thioether. Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT) groups.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"$(C_3-C_8)$aryl-$(C_1-C_6)$alkylene" refers to a divalent alkylene wherein one or more hydrogen atoms in the $C_1-C_6$ alkylene group is replaced by a $(C_3-C_8)$aryl group. Examples of $(C_3-C_8)$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene. The term "$(C_3-C_8)$cycloalkyl-$(C_1-C_6)$alkylene" refers to a divalent alkylene wherein one or more hydrogen atoms in the $C_1-C_6$ alkylene group is replaced by a $(C_3-C_8)$cycloalkyl group. Examples of $(C_3-C_8)$cycloalkyl-$(C_1-C_6)$alkylene groups include without limitation 1-cycloproylbutylene, cyproyl-2-butylene, cyclopentyl-1-phenyl-2-methylpropylene, cyclobutyhnethylene and cyclohexylpropylene.

An "analog" of a nucleic acid is a composition comprising a sequence of nucleobases arranged on a substrate, such as a polymeric backbone, and is able to bind DNA and/or RNA by hybridization by Watson-Crick, or Watson-Crick-like hydrogen bond base pairing. Non-limiting examples of common nucleic acid analogs include peptide nucleic acids, such as γPNA, morpholino nucleic acids, phosphorothioates, locked nucleic acid (2'-O-4'-C-methylene bridge, including oxy, thio or amino versions thereof), unlocked nucleic acid (the C2'-C3' bond is cleaved), 2'-O-methyl-substituted RNA, threose nucleic acid, glycol nucleic acid, etc.

As indicated above, a method of producing a PNA (e.g., γPNA) oligomer is provided, comprising, binding a plurality of the recognition modules described above, for example as shown in Formula 1, to a template nucleic acid in a reducing environment, e.g., in the presence of a reducing agent. The compositions will ligate once the N-terminal disulfide is cleaved and the terminal thioester and thiol groups are in proximity to each other. The thioester and thiol groups are considered to be in proximity to each other when they are sufficiently close such that the compounds will ligate to each other rather than form an intramolecular bond between ends of the same molecule and thereby circularize (see, FIG. 2). Non-limiting examples of reducing agents include DTT (dithiothreitol), DTE (dithioerythritol), glutathione, and TCEP (tris(2-carboxyethyl)phosphine). In vivo, the reducing agent typically would be glutathione. As indicated above, synthesis of small γPNA oligomers of 3-8 bases is much easier than synthesizing longer oligomers, such that it is expected be more cost-effective to synthesize the long oligomers on a template according to the methods described herein.

Figure 9:
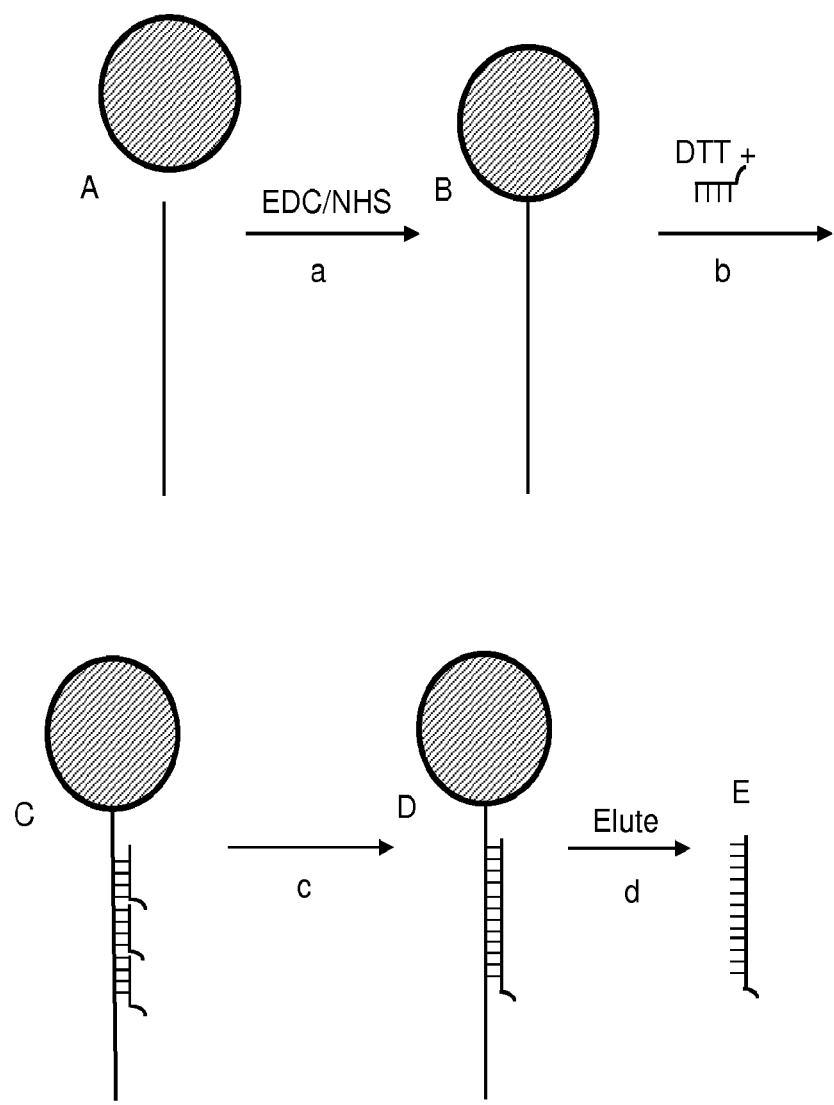
FIG. 9 depicts schematically a non-limiting example of preparation of a γPNA oligomer on a substrate according the methods described herein.

In one embodiment, template nucleic acid is synthesized and is attached to a suitable substrate, such as, without limitation, a polymer/resin bead, a magnetic bead, a polymeric vessel, a lumen of a tube, or a silicon chip as are known in the art. In one example, as shown in FIG. 9, a template nucleic acid is attached to a substrate, specifically in this instance, a polymeric bead comprising agarose or acrylamide (A). In one embodiment, the template may be a PNA, such as a γPNA, or another nucleic acid analog, that exhibits resistance to degradation when used multiple times. Amino-modified templates can be attached to agarose by standard EDC/NHS (1-Ethyl-3-[3-dimethylaminopropyl] carbodiimide hydrochloride/N-hydroxysuccinimide) methods as are well-known in the art (a). According to well-established affinity purification principles, the bead can be maintained in a slurry or column, and, when not in a column, can be washed and separable by standard methods including filtration or centrifugation. In many instances, a column is a preferred method of managing the beads. In use, the oligomers described herein, for example as shown in Formula 1, are contacted (b) with the substrate-bound template (B) in the presence of a reducing agent, such as DTT, TCEP or glutathione, cleaving the N-terminal protective group, leaving a free thiol. The recognition modules bind specifically with the template (C). Recognition modules ligate together (c), to form a longer oligomeric structure (D). As indicated above, the oligomers affixed to the template and ligated can all have the same sequence and length, or can be of different sequences and lengths. Once the oligomer fragments are ligated, the column, and beads are washed one or more time (d) and the ligation product (E) is eluted from the beads, e.g., by salt elution, and can be isolated and purified from the elution mixture by standard methodologies. The beads are then washed and readied for re-use. An essentially identical protocol can be used for any substrate to which the template is bound, such on the lumen of tubes, a planar surface, beads, porous surfaces, meshes, etc.

In another method, the oligomers described herein, for example in Formula 1, are introduced into a cell. A variety of methods for delivery of a nucleic acid or analog thereof are well-known in the biological, pharmaceutical and medical arts. A variety of transfection reagents, suitable for in vitro or in vivo use are known in the art and are suitable for delivery of the compositions described herein to cells, such as FuGENE®, or liposomal preparations (commercially available from multiple sources, See, also, Immordino et al. "Stealth liposomes: review of the basic science, rationale, and clinical applications, existing and potential," (2006) *Int'l J. Nanomedicine* 1(3):297-316). Once within the cells, the compounds, e.g. the compound of Formula 1, will hybridize specifically to a nucleic acid template. When more than one of the recognition modules hybridize to the same template nucleic acid, placing the thiol and thioester end-groups in proximity to each-other, the recognition modules will ligate due to the presence of a reducing agent, such as glutathione, in the cell, releasing the N-terminal thiol by cleavage of the disulfide protective group. Compounds that do not bind a nucleic acid containing either repeats of the recognition module's sequence, or adjacent sequences complementary to more than one of the delivered recognition modules will release from the bound nucleic acid because the strength of the binding of the 3-8-mer is not strong enough to maintain the compound on the bound nucleic acid. When more than one recognition module binds to a target nucleic acid sequence, they will ligate and form an oligomer, or polymer of sufficient length to bind the nucleic acid with sufficient strength to remain hybridized to the target sequence, for achieving a desired effect, such as gene silencing where the composition has a sequence of an siRNA, miRNA, mirtron or similar composition. Recognition modules will eventually form a self-deactivated cyclic structure as depicted in FIG. 2B if it cannot bind to a target sequence and ligate to a second recognition module.

According to yet another embodiment, a composition is provided comprising any embodiment of the recognition modules described herein combined with a transfection reagent as described herein, such as a liposome. The composition optionally comprises a pharmaceutically acceptable carrier, such as, without limitation, water, saline and buffered saline. The composition is typically sterilized by any useful method, such as ultrafiltration, gamma radiation, or any other method that does not affect the function of the compositions as described herein. In another embodiment a kit is provided, including one or more recognition modules as described herein in a vessel, which is any suitable container, including a cartridge for use in an automatic dispensing system, for example as part of an automated system for carrying out any method as described herein. A cartridge may comprise multiple vessels in the form of compartments. The kit may contain additional recognition modules, liposomes, reducing agents, template nucleic acids, optionally bound to a substrate, column(s), etc.

EXAMPLE 1

Synthesis of γPNA Recognition Modules

γPNA1 and γPNA2 were synthesized according to exemplary schemes 1 and 2, as indicated above, with the exception of the substitution of nucleobase analogue (X) (see FIG. 3).

EXAMPLE 2

Reduction Recognition Module in Reducing Environment

Figure 10:
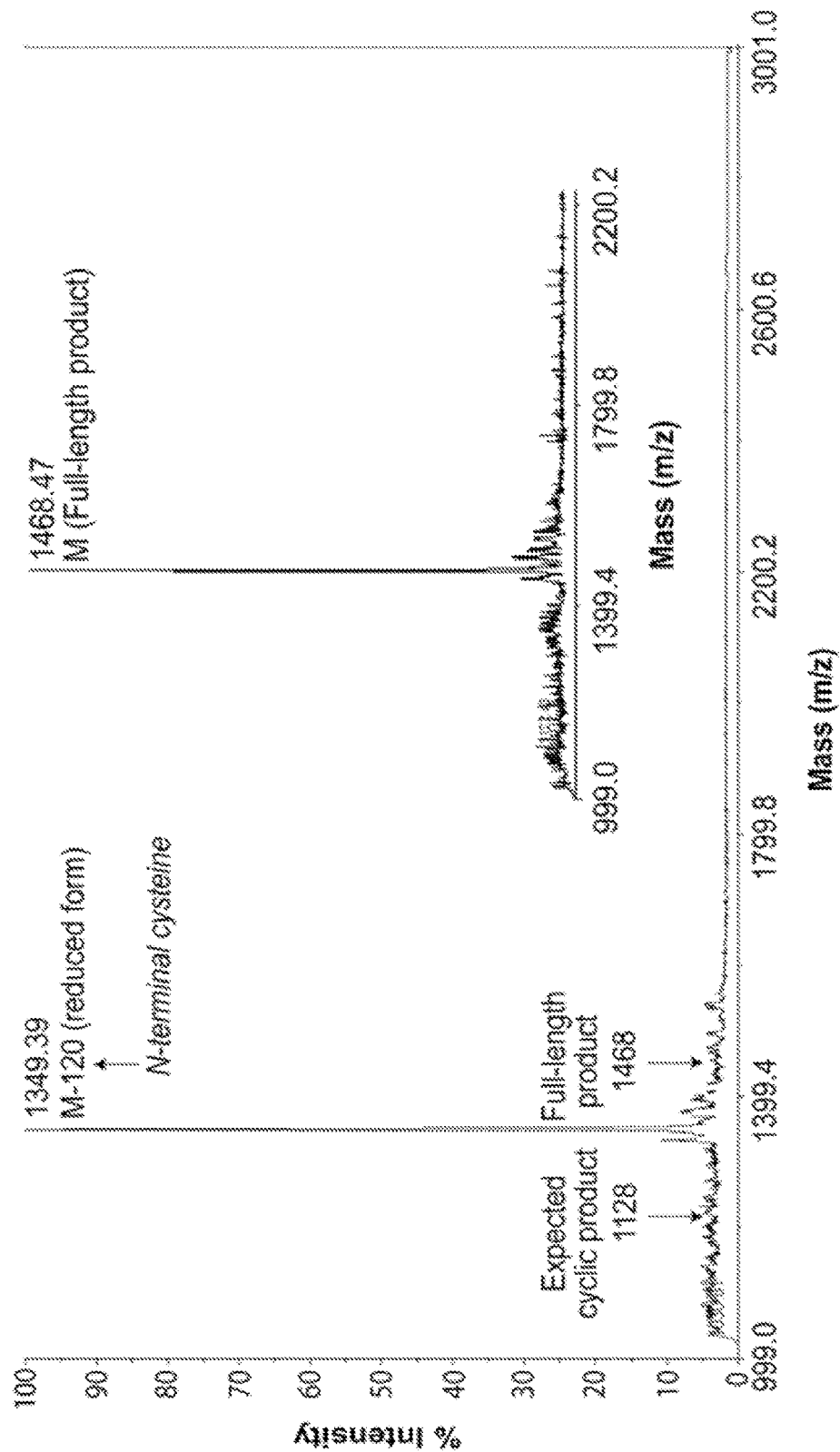
FIG. 10: shows a MALDI-TOF mass spectrum of γPNA1 after incubation with 10 mM DTT at room temperature (24° C.) for 1 hr. There is complete reduction of the disulfide bond (m/z: 1349.39) and no cyclized product was observed (m/z: 1128.39). Inset: MALDI-TOF mass spectrum of γPNA1 before reduction.

In one embodiment, γPNA1 recognition module synthesized as in Schemes 1 and 2. γPNA1 was incubated in simulated physiological buffer (10 mM NaPi, 150 mM KCl, 2 mM MgCl$_2$) with 10 mM DTT at room temperature. Results are illustrated in FIG. 10, with the spectrum for the compound prior to reduction shown in the inset. There is complete reduction of the disulfide bond (m/z: 1349.39) and no cyclized product was observed (m/z: 1128.39). These results demonstrate that the disulfide bond can be readily reduced and no cyclization takes place within 1 hr at room temperature in a simulated physiological buffer (10 mM NaPi, 150 mM KCl, 2 mM MgCl$_2$).

Figure 11A:
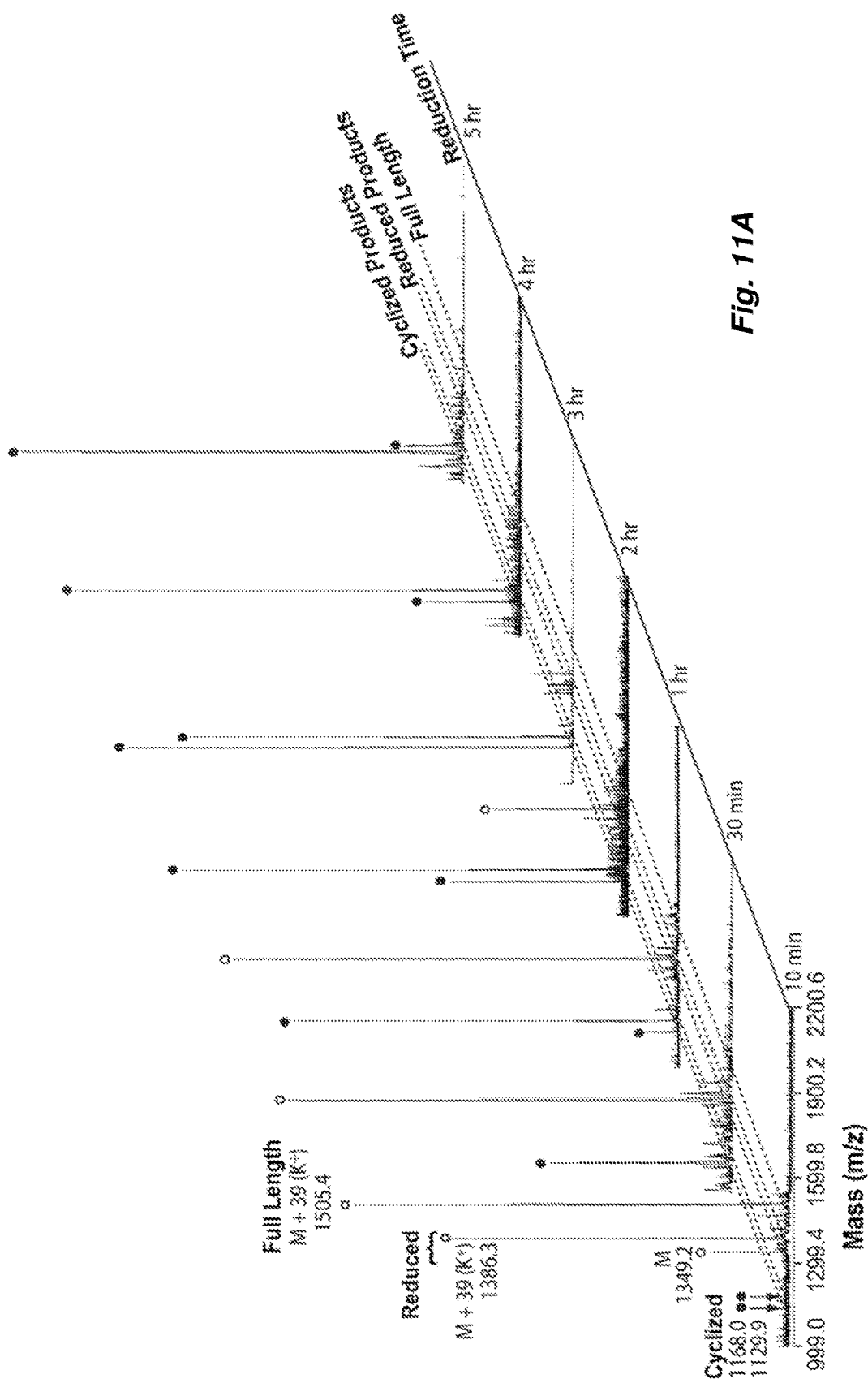
FIGS. 11A and 11B illustrate a comparison of the rates of reduction (disulfide bond cleavage) vs. cyclization of γPNA1 (FIG. 11A) and γPNA2 (FIG. 11B) upon incubation with 10 mM TCEP at 37° C. at the indicated time-points. The difference between the two oligomers is that γPNA2 contained an expanded cytosine nucleobase analogue (X) at the N terminus, whereas γPNA1 contained cytosine.
Figure 11B:
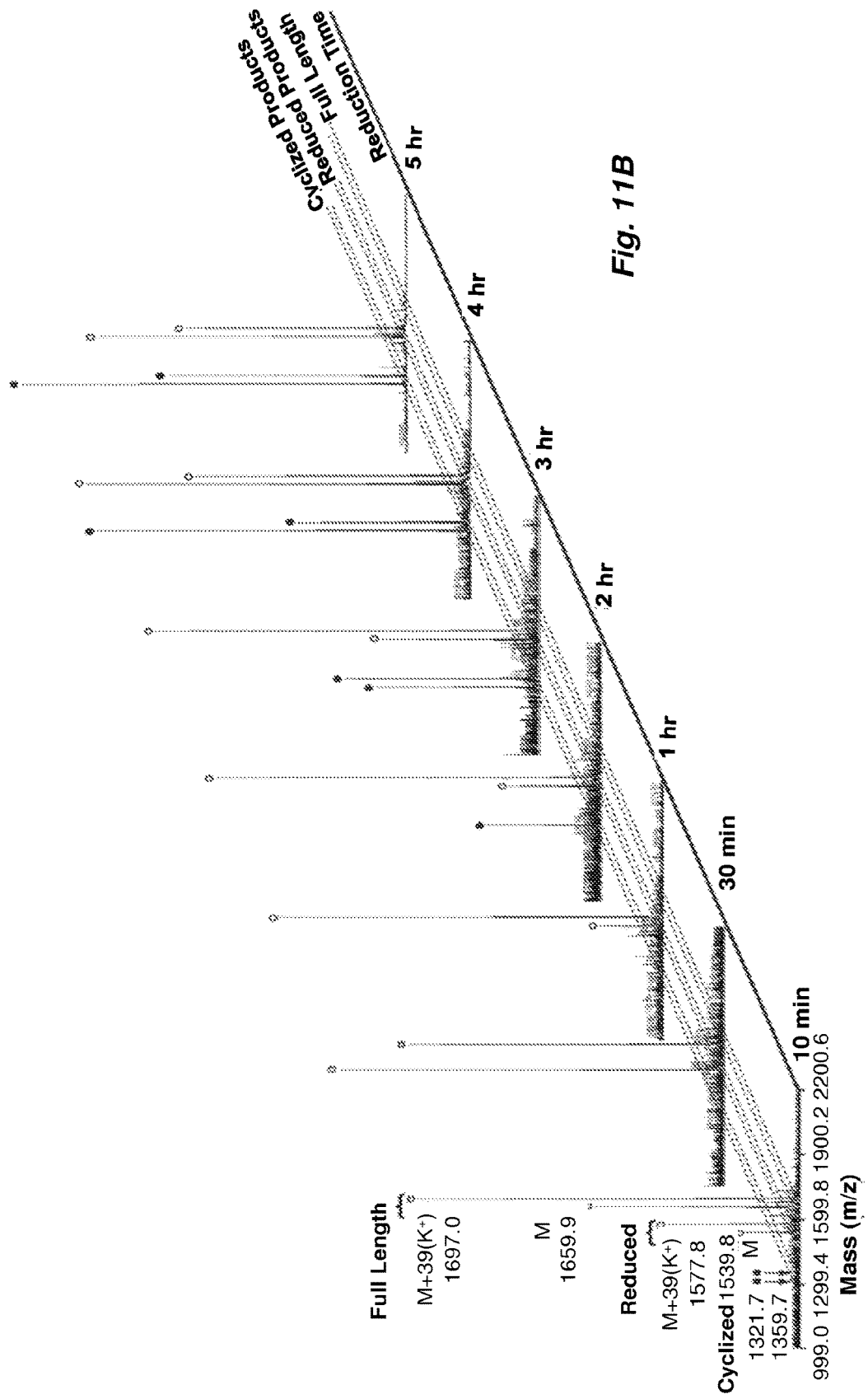

Additionally, the rates of reduction (disulfide bond cleavage) vs. cyclization of γPNA1 and γPNA2 (see, FIGS. 11A and 11B, respectively) was determined upon incubation with 10 mM TCEP (tris(2-carboxyethyl)phosphine) in a simulated physiological buffer (10 mM sodium phosphate, 2 mM MgCl$_2$, 150 mM KCl, pH 7.4) at 37° C. at various time points. γPNA1 and γPNA2 are shown in FIG. 3. The difference between the two oligomers is that γPNA2 contained the expanded cytosine nucleobase analogue (X) at the N terminus, whereas γPNA1 contained cytosine. This result indicates that cyclization occurs at physiological temperature (37° C.) but at a rate that is much slower than that of the unmodified PNA (spontaneous). The half-life for cyclization of γPNA1 and γPNA2 are ~1-hr and 4-hr, respectively—indicating that the better the base-stacking (larger aromatic ring size), the slower the rate of cyclization. This result shows that the rate of cyclization at physiologically relevant temperature (37° C.) and ionic strength is relatively slow as compared to the rate of reduction and can be fine-tuned by varying the degree of base-stacking or aromatic ring size of the recognition elements.

EXAMPLE 3

Melting Profile with Template (Target) RNA

Figure 12:
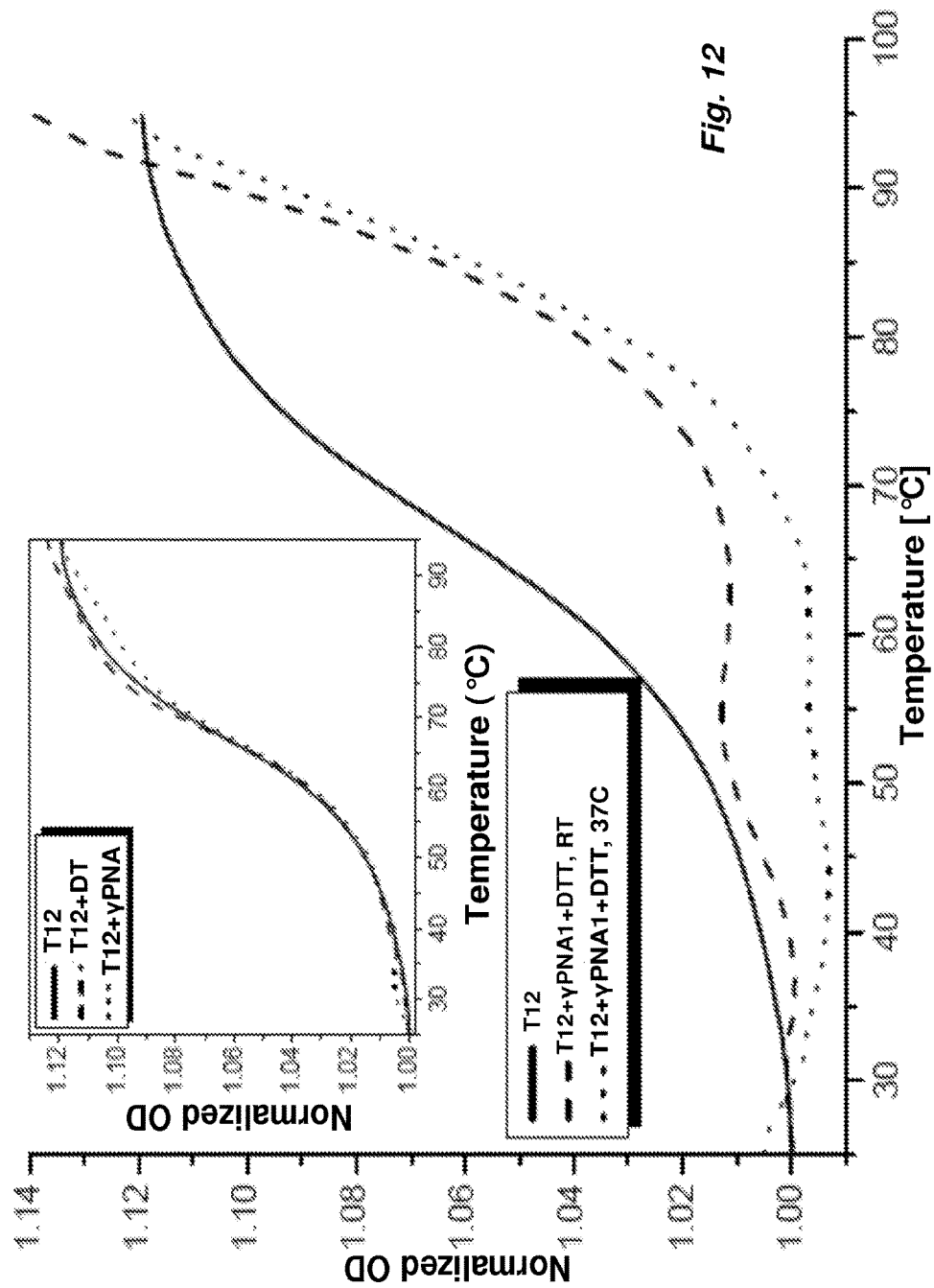
FIG. 12 illustrates the UV-melting profiles of RNA target T12 alone (solid line), and T12 with γPNA1 and DTT (10 mM) at room temperature and at 37° C.

In another example, the UV-melting profiles of the γPNA1 probe incubated with target RNA T12 were determined and the results are illustrated in FIG. 12. DTT or γPNA1 alone had no effect on the melting transition of T12 (FIG. 12, Inset). This result shows that γPNA1 is able to bind to the T12 target and initiate the template directed 'native chemical ligation' reaction to form longer oligomers and hybridize to the designated target, as demonstrated by the higher melting transitions.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A method of producing PNA oligomers, comprising contacting a template nucleic acid in a reducing environment, with a plurality of recognition modules of Formula 1,

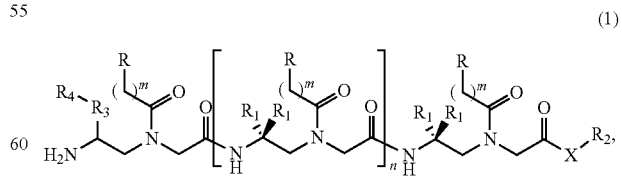

(1)

in which,

X is S or O;

n is an integer from 1 to 6, inclusive;

m is an integer from 0 to 4, inclusive;

each instance or R1 is attached to a gamma carbon, and independently is selected from the group consisting of H,

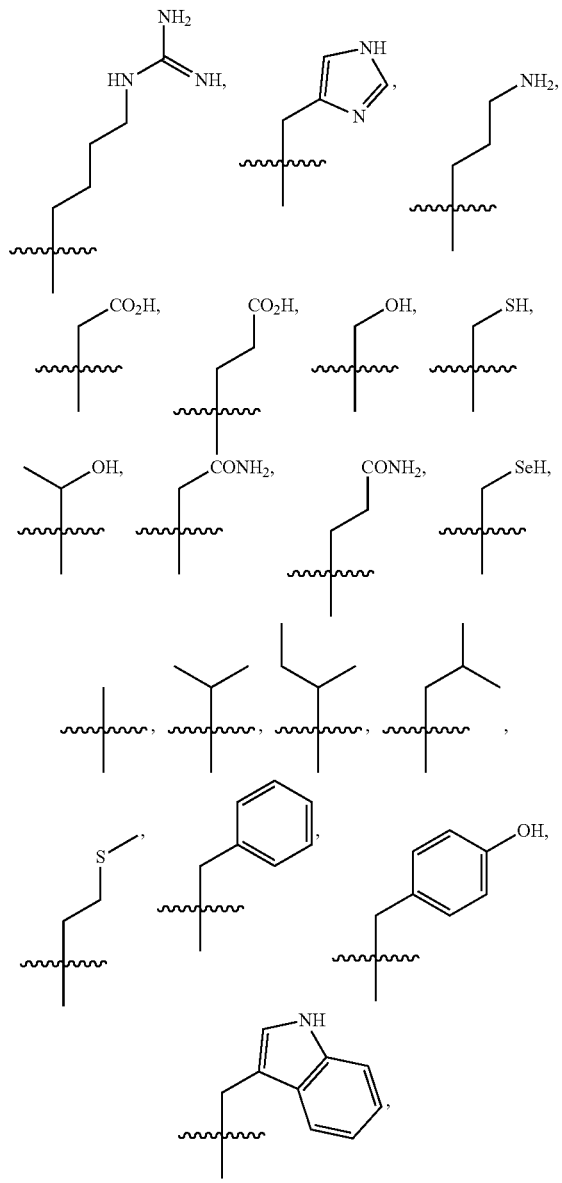

linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, $-CH_2-(OCH_2-CH_2)_q-OP_1$, $-CH_2-(OCH_2-CH_2)_q-NHP_1$, $-CH_2-(OCH_2-CH_2-O)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S[CH_2CH_2]_sNHC(NH)NH_2$, where $P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene and $(C_3-C_8)$cycloalkyl$(C_1-C_6)$alkylene;

q is an integer from 0 to 50, inclusive;

r and s are each independently integers from 1 to 50, inclusive;

R2 is selected from the group consisting of H, linear or branched $(C_1-C_8)$alkyl, substituted or unsubstituted $(C_3-C_8)$aryl, $(C_3-C_8)$aryl$(C_1-C_6)$alkylene, $(C_1-C_8)$ carboxylic, or

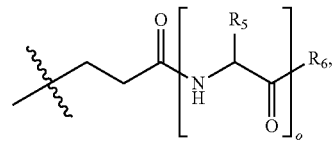

where o is 1-20, each instance of R5 is, independently,

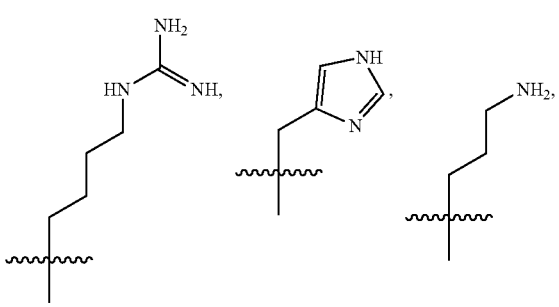

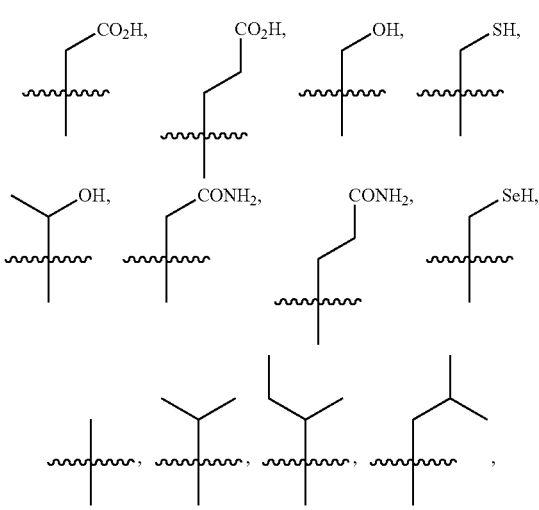

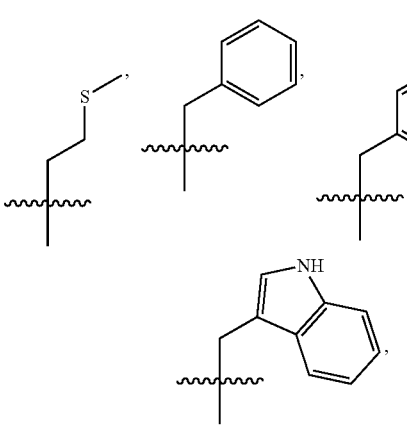

and R6 is $-OH$ or $NH_2$;

R3 is ($C_1$-$C_{10}$) divalent hydrocarbon or ($C_1$-$C_{10}$) divalent hydrocarbon substituted with one or more N or O moieties;

R4 is —OH, —SH or a disulfide protecting group; and each instant of R, for each of the plurality of recognition modules is, independently, a nucleobase, producing a sequence of nucleobases complementary to a target sequence of nucleobases in the template nucleic acid so that each of the plurality of recognition modules bind to the target sequence of nucleobases on the template nucleic acid and ligate to each other.

2. The method of claim 1, in which the template nucleic acid is DNA or RNA.

3. The method of claim 1, in which the template nucleic acid is a nucleic acid analog.

4. The method of claim 1, in which the template nucleic acid is attached to a substrate.

5. The method of claim 4, in which the substrate is a bead.

6. The method of claim 4, comprising:
    a. contacting the plurality of recognition molecules with the template nucleic acid;
    b. exposing the recognition molecules bound to the template nucleic acid to a reducing agent, thereby causing the recognition molecules bound to the template nucleic acid to ligate together to produce an extended γPNA oligomer; and
    c. eluting the γPNA oligomer from the template nucleic acid.

7. The method of claim 6, in which the method is performed in a column retaining the substrate and template nucleic acid.

8. The method of claim 1, in which the reducing environment is produced by a reducing agent.

9. The method of claim 1, in which the recognition modules have the same sequence and are complementary to a tandemly-repeated nucleobase sequence in the target nucleic acid.

10. The method of claim 1, in which the sequence of nucleobases R for the recognition modules is selected from the group consisting of, from 5' to 3': GAA, CGG, CCG, CAG, CTG, CCTG, ATTCT, and GGGGCC or a sequence complementary thereto.

11. The method of claim 1, in which R4 has the structure —SH, —OH, or —S—R7, where R7 is one or more amino acid residues,

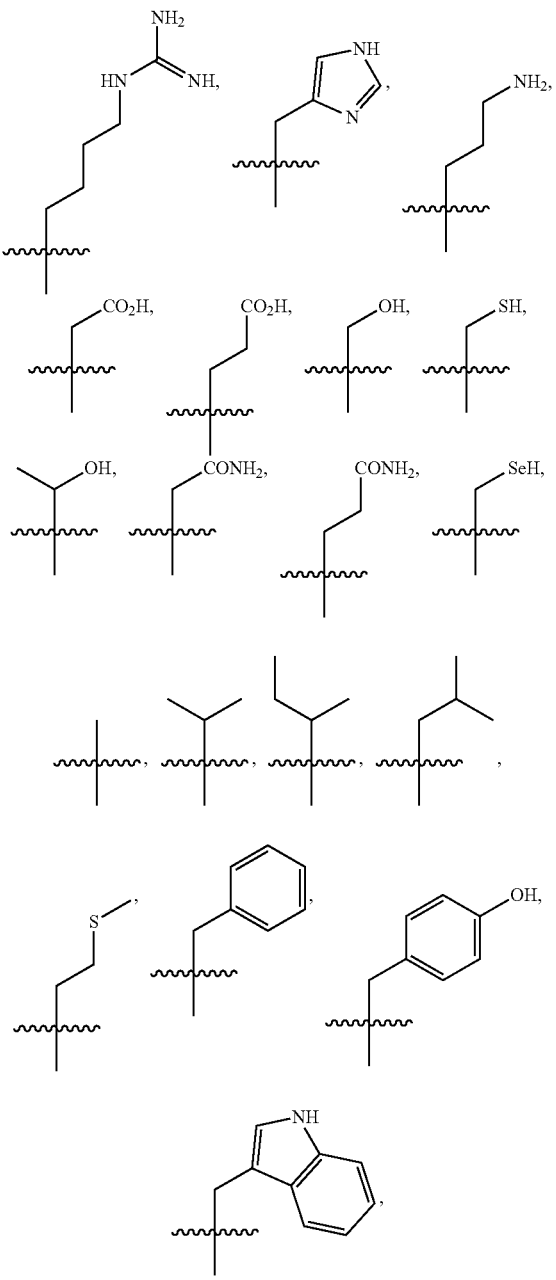

linear, branched, or hetero-substituted ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, or ($C_3$-$C_8$)cycloalkyl($C_1$-$C_6$)alkylene.

12. The method of claim 1, in which recognition module has the structure of Formula 2:

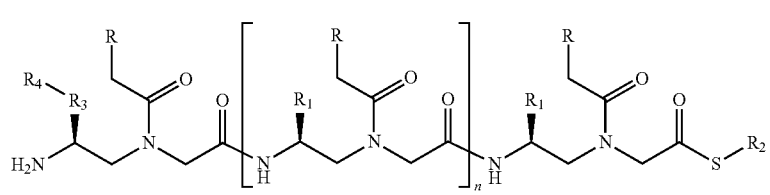

(2)

in which, each instance of R1 is independently

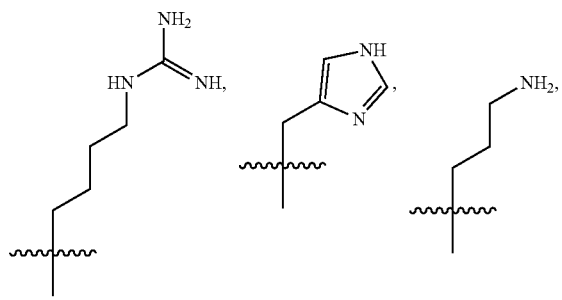

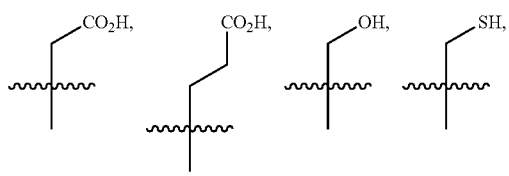

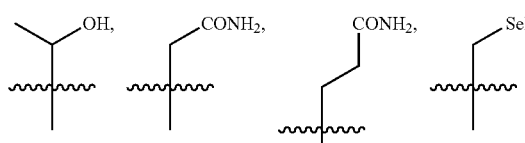

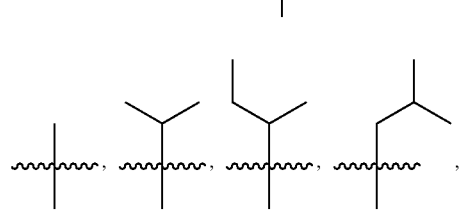

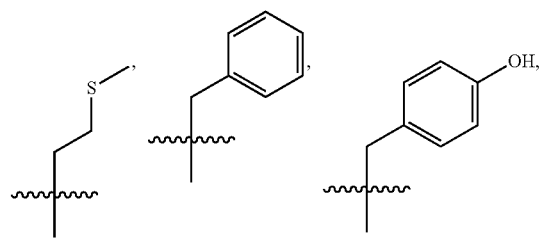

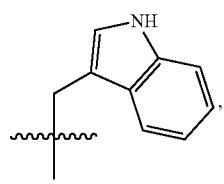

—CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where r and s are each independently 1-50;

R2 is selected from the group consisting of H, linear or branched (C$_1$-C$_8$)alkyl, substituted or unsubstituted (C$_3$-C$_8$)aryl, (C$_3$-C$_8$)aryl(C$_1$-C$_6$)alkylene, (C$_1$-C$_8$) carboxylic, or

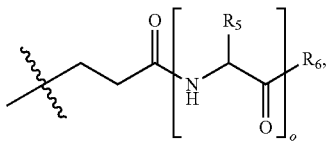

where o is 1-20, each instance of R5 is independently an amino acid side chain, and R6 is —OH or NH$_2$; and each instance of R is independently, a nucleobases.

13. The method of claim 1, in which R4 is —OH.

14. The method of claim 1, in which R4 is —SH.

15. The method of claim 1, in which one or more instances of R are selected from the group consisting of

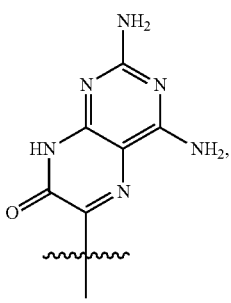
(JB1)

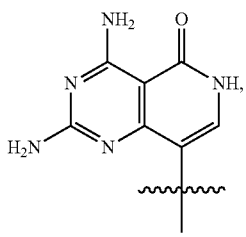
(JB2)

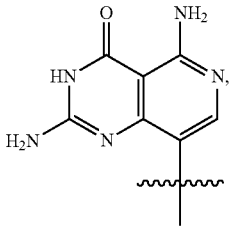
(JB3)

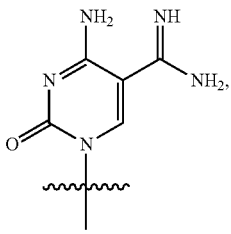
(JB4)

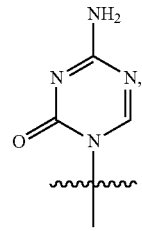
(JB5)

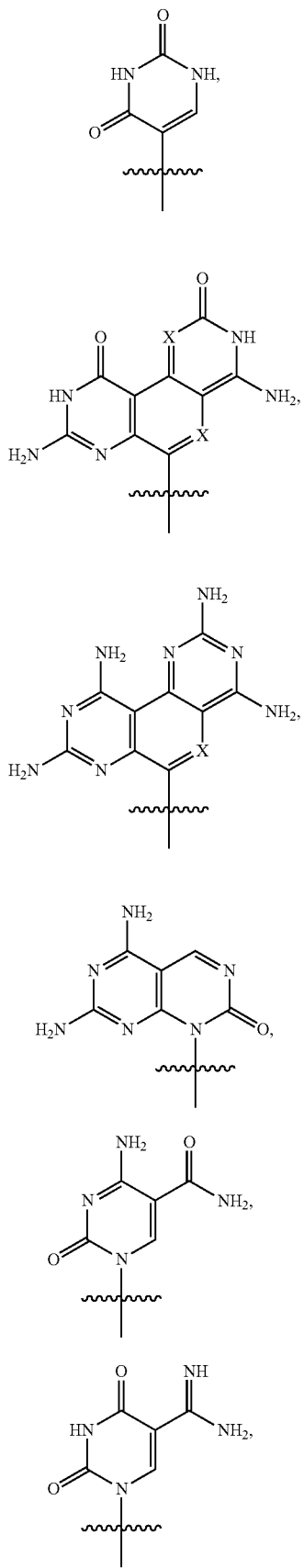

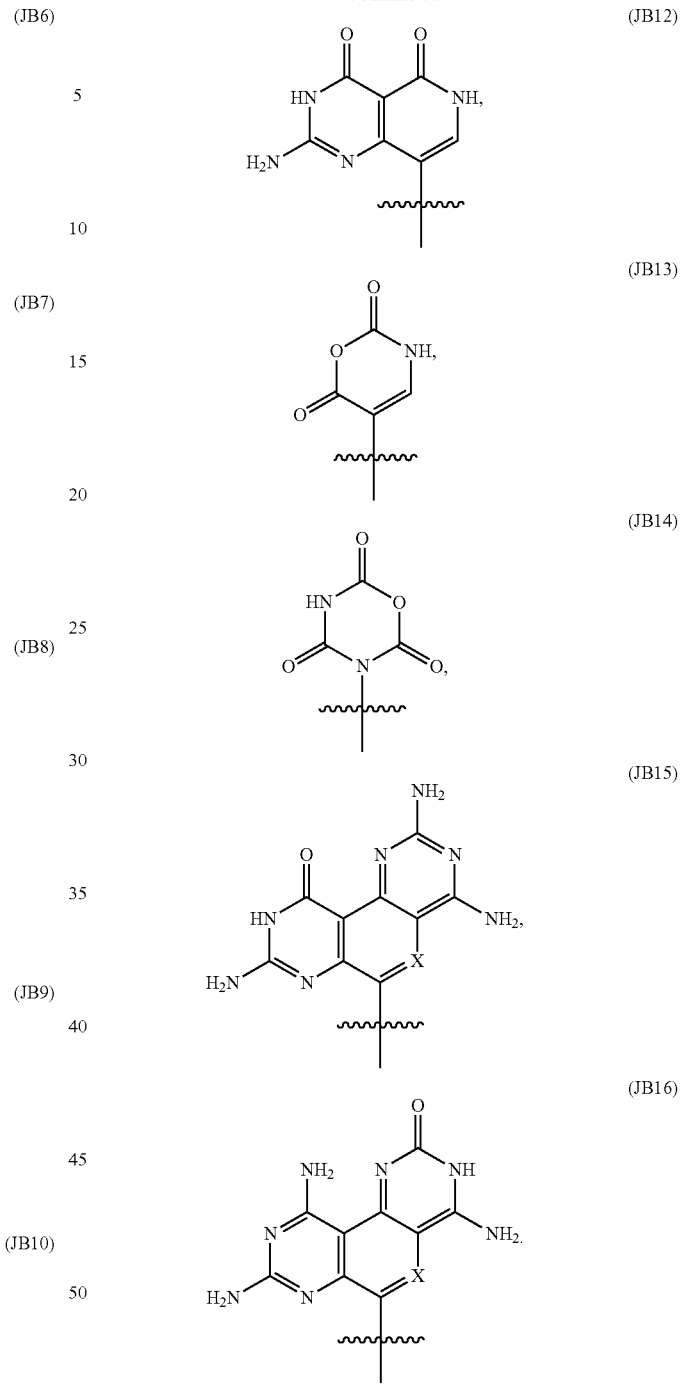

16. The method of claim 1, in which one or more instances of R are selected from the group consisting of adenine, guanine, thymine, cytosine, uracil, hypoxanthine, xanthene, 7-methylguanine, 5, 6, dihydrouracil, 5-methylcytosine, and 5-hydroxymethylcytosine.

17. The method of claim 1, in which one or more instances of R are selected from the group consisting of a nucleobase of FIG. 4A.

18. The method of claim 1, in which nucleobases R of both of the plurality of recognition modules are arranged in a sequence complementary to target sequences of the template nucleic acid so that each of the plurality of recognition modules bind to sequences of bases on the template nucleic acid and ligate to each other.

19. The method of claim 1, in which nucleobases R of the plurality of recognition modules are arranged in a sequence complementary to adjacent portions of a contiguous target sequence of nucleobases of the template nucleic acid so that each of the plurality of recognition modules bind adjacent to each other on the contiguous target sequence of nucleobases on the template nucleic acid.

20. The method of claim 1, in which the sequence of nucleobases R for each of the plurality of recognition modules is the same.

21. The method of claim 1, in which at least one instance of R1 is an amino acid side chain.

22. The method of claim 1, in which at least one instance of R1 for each gamma carbon is an H.

23. The method of claim 1, in which for each gamma carbon, one instance of R1 is an H and the other is an amino acid side chain, and each gamma carbon has the same amino acid side chain at R1.

24. A composition having the structure of Formula 1,

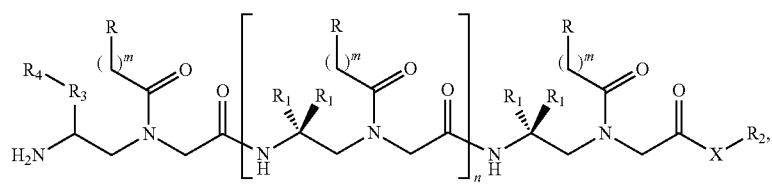

(1)

in which,

X is S or O;

n is an integer from 1 to 6, inclusive;

m is an integer from 0 to 4, inclusive;

each instance of R1 is attached to a gamma carbon, and independently is selected from the group consisting of H,

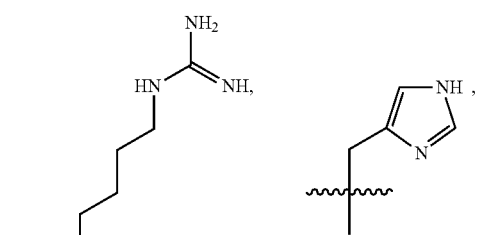

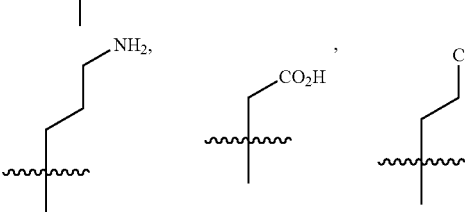

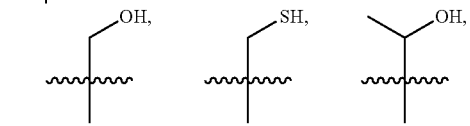

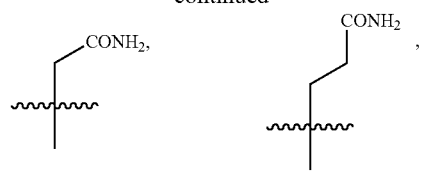

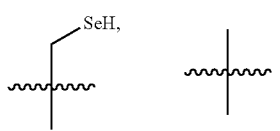

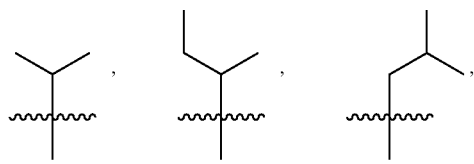

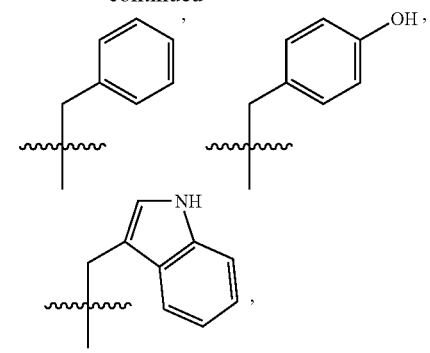

linear or branched $(C_1$-$C_8)$alkyl, $(C_2$-$C_8)$alkenyl, $(C_2$-$C_8)$alkynyl, $(C_1$-$C_8)$hydroxyalkyl, $(C_3$-$C_8)$aryl, $(C_3$-$C_8)$cycloalkyl, $(C_3$-$C_8)$aryl$(C_1$-$C_6)$alkylene, $(C_3$-$C_8)$cycloalkyl$(C_1$-$C_6)$alkylene, —$CH_2$—$(OCH_2$—$CH_2)_q$—$OP_1$, —$CH_2$—$(OCH_2$—$CH_2)_q$—$NHP_1$, —$CH_2$—$(OCH_2$—$CH_2$—$O)_q$—$SP_1$ and —$CH_2$—$(SCH_2$—$CH_2)_q$—$SP_1$, —$CH_2$—$(OCH_2$—$CH_2)_r$—$OH$, —$CH_2$—$(OCH_2$—$CH_2)_r$—$NH_2$, —$CH_2$—$(OCH_2$—$CH_2)_r$—$NHC(NH)NH_2$, or —$CH_2$—$(OCH_2$—$CH_2)_r$—$S$—$S[CH_2CH_2]_s NHC(NH)NH_2$, where $P_1$ is selected from the group consisting of H, $(C_1$-$C_8)$alkyl, $(C_2$-$C_8)$alkenyl, $(C_2$-$C_8)$alkynyl, $(C_3$-$C_8)$aryl, $(C_3$-$C_8)$cycloalkyl, $(C_3$-$C_8)$aryl$(C_1$-$C_6)$alkylene and $(C_3$-$C_8)$cycloalkyl$(C_1$-$C_6)$alkylene;

q is an integer from 0 to 50, inclusive;

r and s are each independently integers from 1 to 50, inclusive;

R2 is selected from the group consisting of H, linear or branched $(C_1-C_8)$alkyl, substituted or unsubstituted $(C_3-C_8)$aryl, $(C_3-C_8)$aryl$(C_1-C_6)$alkylene, $(C_1-C_8)$ carboxylic, or

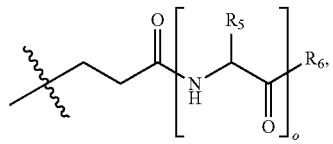

where o is 1-20, each instance of R5 is, independently,

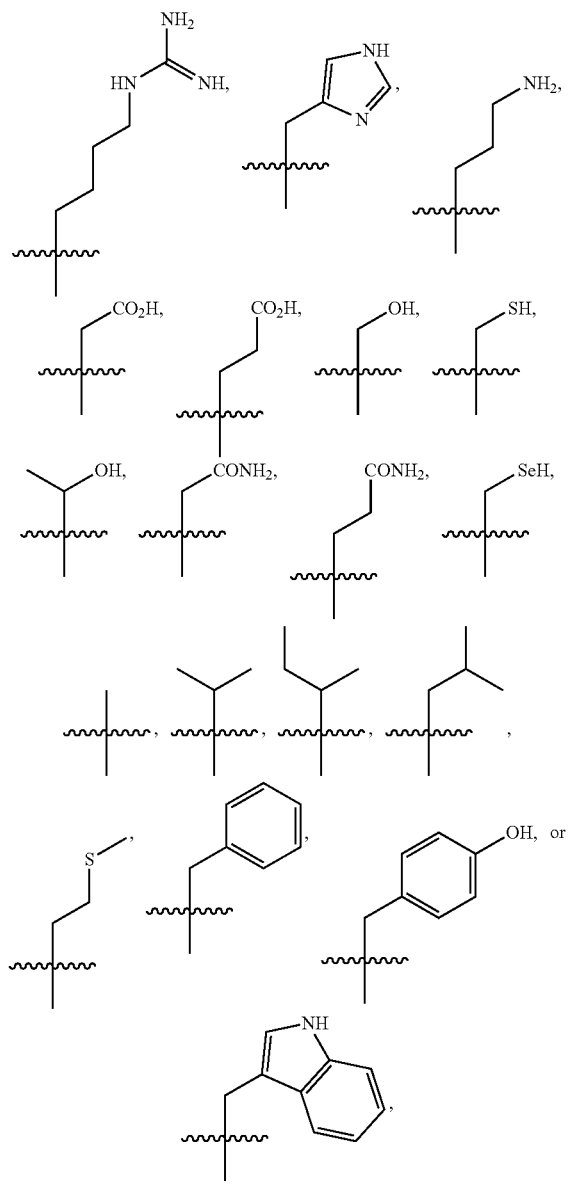

and R6 is —OH or $NH_2$;

R3 is $(C_1-C_{10})$ divalent hydrocarbon or $(C_1-C_{10})$ divalent hydrocarbon substituted with one or more N or O moieties;

R4 is —SH or a disulfide protecting group; and each instance of R is, independently, a nucleobase, producing a sequence of nucleobases, forming a recognition module, and wherein the recognition module binds to a target sequence of nucleobases on a template nucleic acid and ligates in a reducing environment to one or more recognition modules adjacent to the recognition module on the nucleic acid sequence.

25. The composition of claim 24, in which the sequence of nucleobases R are complementary to a target sequence of nucleobases in a template nucleic acid.

26. The composition of claim 24, in which the sequence of nucleobases R for the recognition module is selected from the group consisting of, from 5' to 3': GAA, CGG, CCG, CAG, CTG, CCTG, ATTCT, GGGGCC, or a sequence complementary thereto.

27. The composition of claim 24, in which R4 has the structure —SH, or —S—R7, where R7 is one or more amino acid residues,

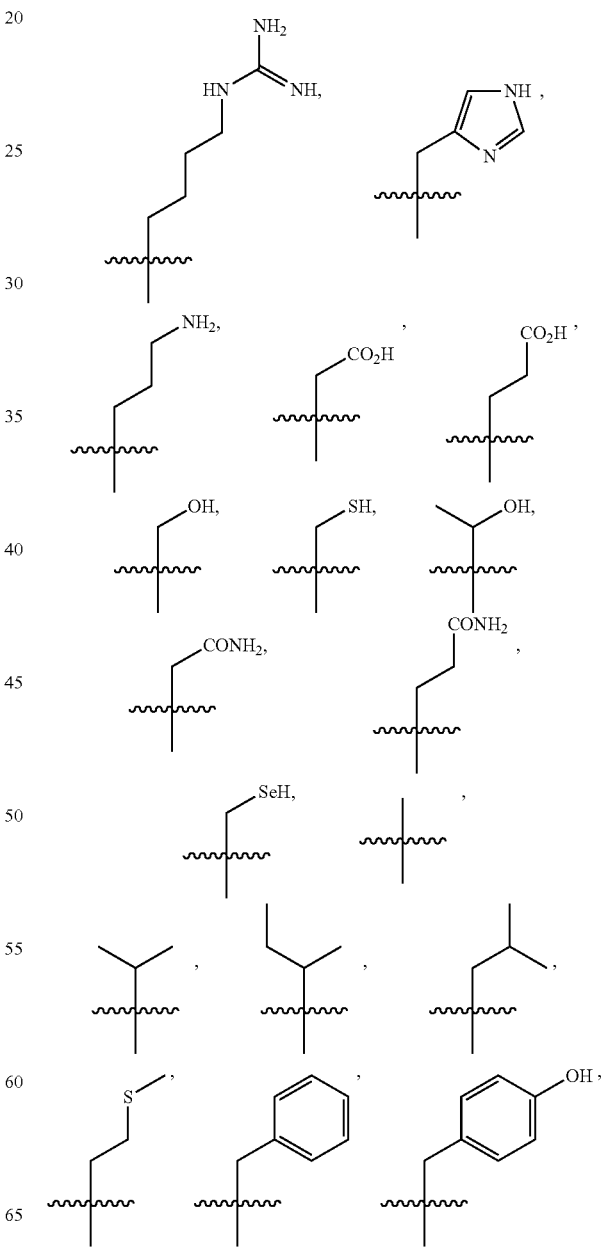

-continued

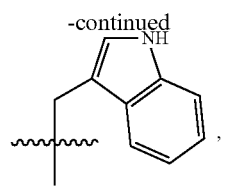, linear, branched or hetero-substituted (C₁-C₈)alkyl, (C₂-C₈)alkenyl, (C₂-C₈)alkynyl, (C₁-C₈)hydroxyalkyl, (C₃-C₈)aryl, (C₃-C₈)cycloalkyl, (C₃-C₈)aryl(C₁-C₆)alkylene, or (C₃-C₈)cycloalkyl(C₁-C₆)alkylene.

28. The composition of claim 24, having the structure of Formula 2:

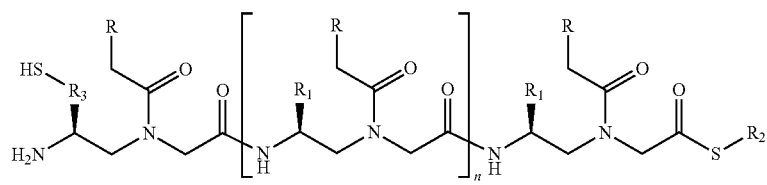

(2)

in which n is 1-6;
each instance of R1 is, independently,

-continued

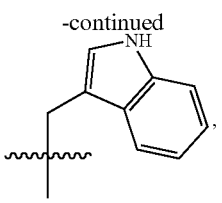,

—CH₂—(OCH₂—CH₂)ᵣ—OH, —CH₂—(OCH₂—CH₂)ᵣ—NH₂, —CH₂—(OCH₂—CH₂)ᵣ—NHC(NH)NH₂, or —CH₂—(OCH₂—CH₂)ᵣ—S—S[CH₂CH₂]ₛNHC(NH)NH₂, where r and s are each independently 1-50; and R2 is selected from the group consisting of H, linear or branched (C₁-C₈)alkyl, substituted or unsubstituted (C₃-C₈)aryl, (C₃-C₈)aryl(C₁-C₆)alkylene, (C₁-C₈) carboxylic, or where o is 1-20, each instance of R5 is, independently,

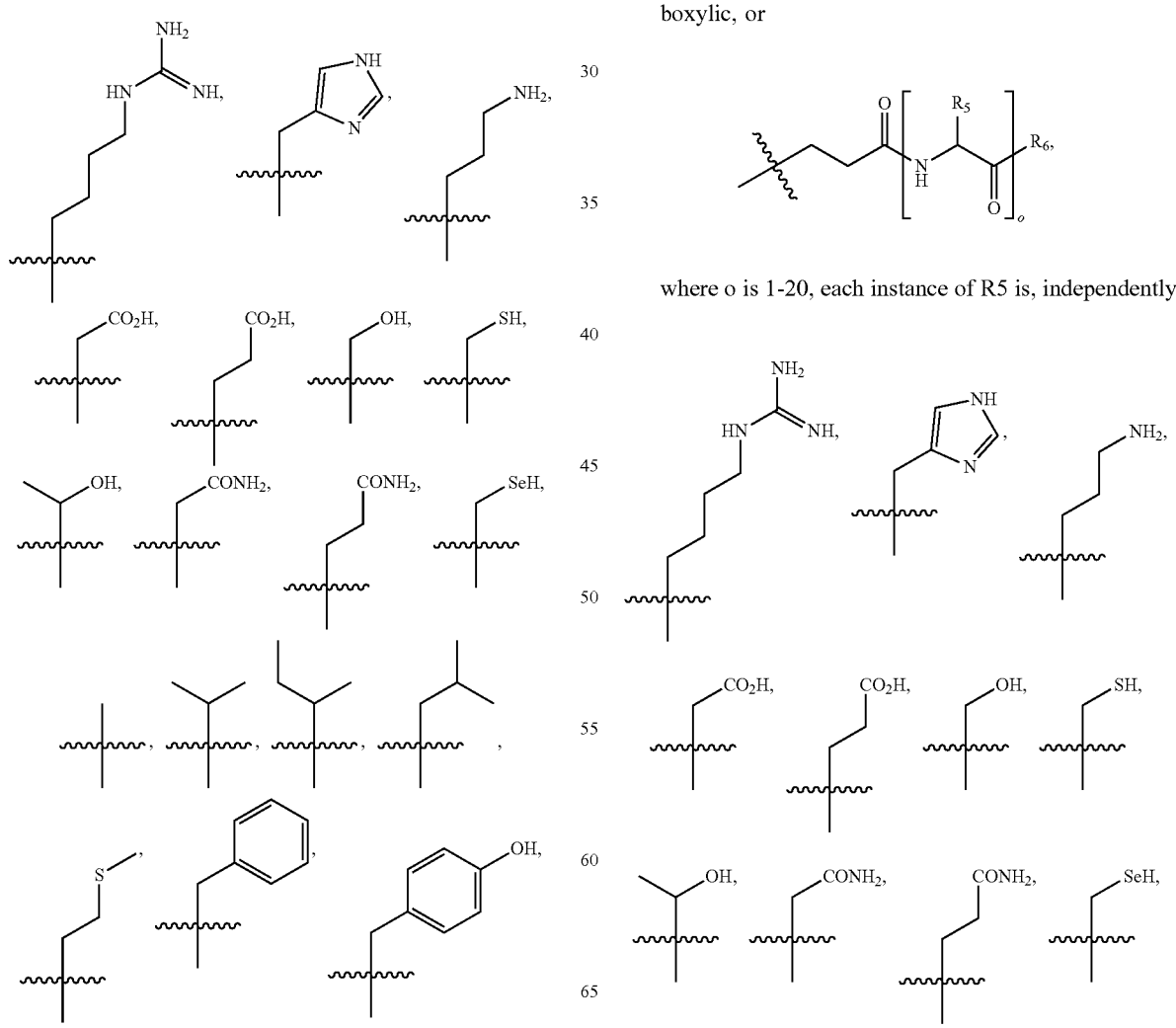

-continued
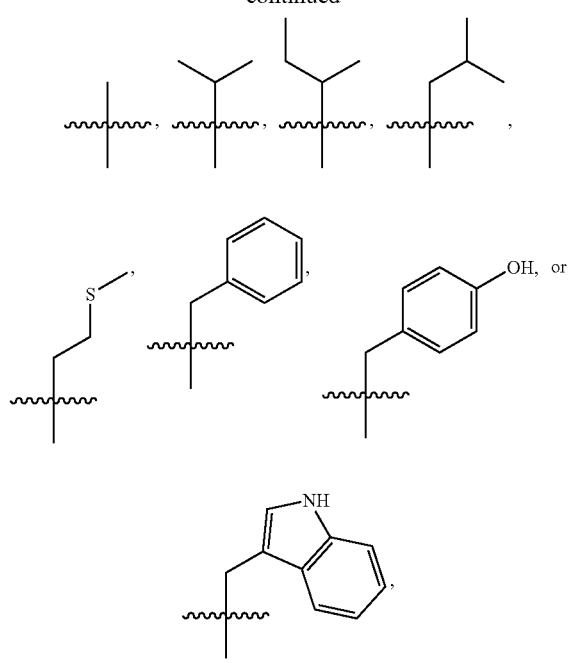
and R6 is —OH or NH$_2$.
29. The composition of claim 24, in which R4 is —SH.
30. The composition of claim 24, in which one or more instances of R are selected from the group consisting of
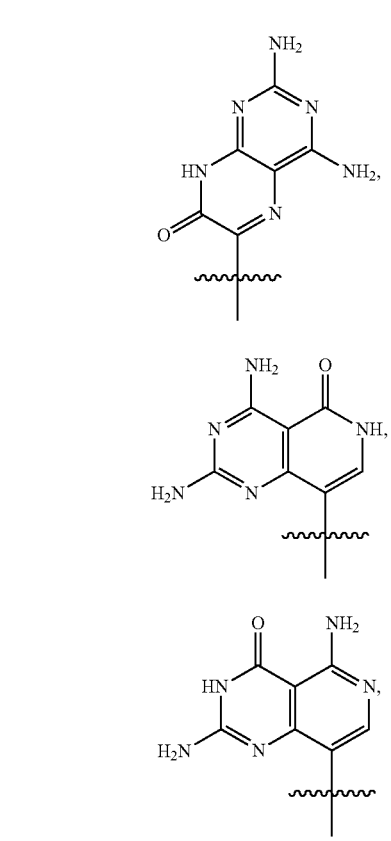
-continued
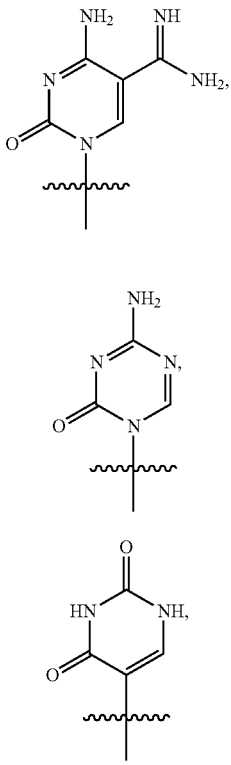
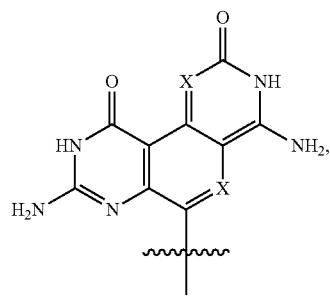
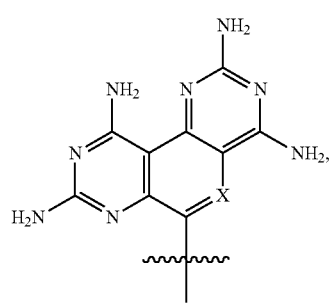
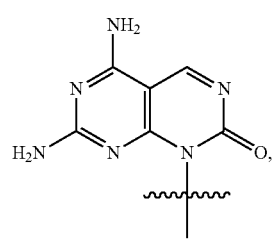

41
-continued (JB10)
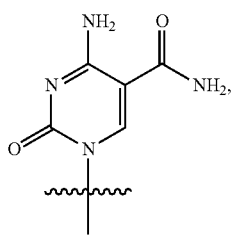

(JB11)
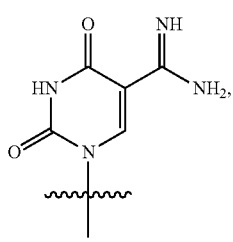

(JB12)
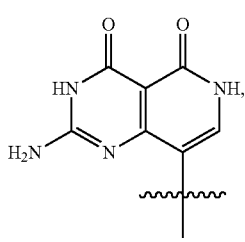

(JB13)
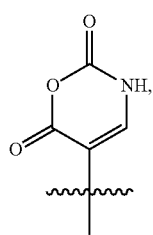

(JB14)
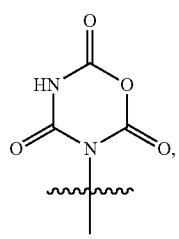

(JB15)
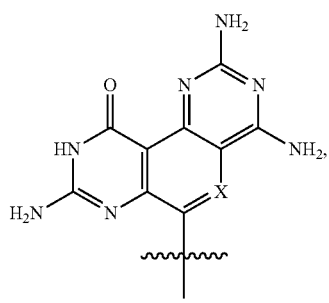

42
-continued (JB16)
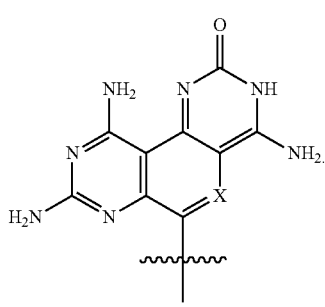

31. The composition of claim 24, in which one or more instances of R are selected from the group consisting of adenine, guanine, thymine, cytosine, uracil, hypoxanthine, xanthene, 7-methylguanine, 5, 6, dihydrouracil, 5-methyl-cytosine, and 5-hydroxymethylcytosine.

32. The composition of claim 24, in which one or more instances of R is selected from the group consisting of a nucleobase of FIG. 4A.

33. The composition of claim 24, in which at least one instance or R1 is

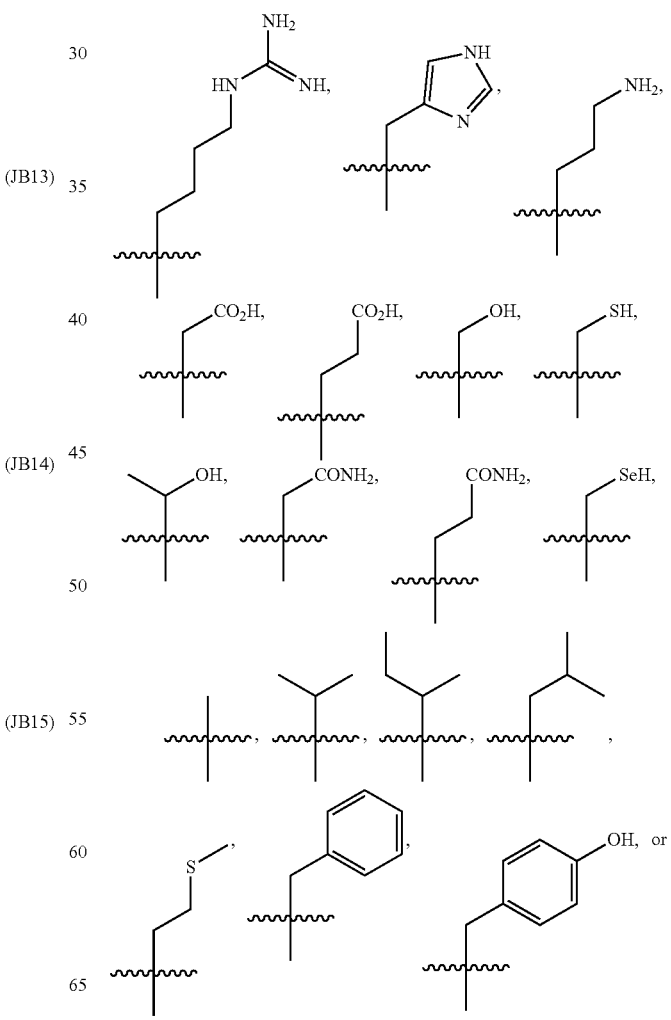

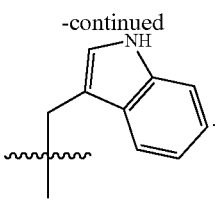

34. The composition of claim 24, in which at least one instance of R1 for each gamma carbon is an H.

35. The composition of claim 24, in which for each gamma carbon, one instance of R1 is an H and the other is

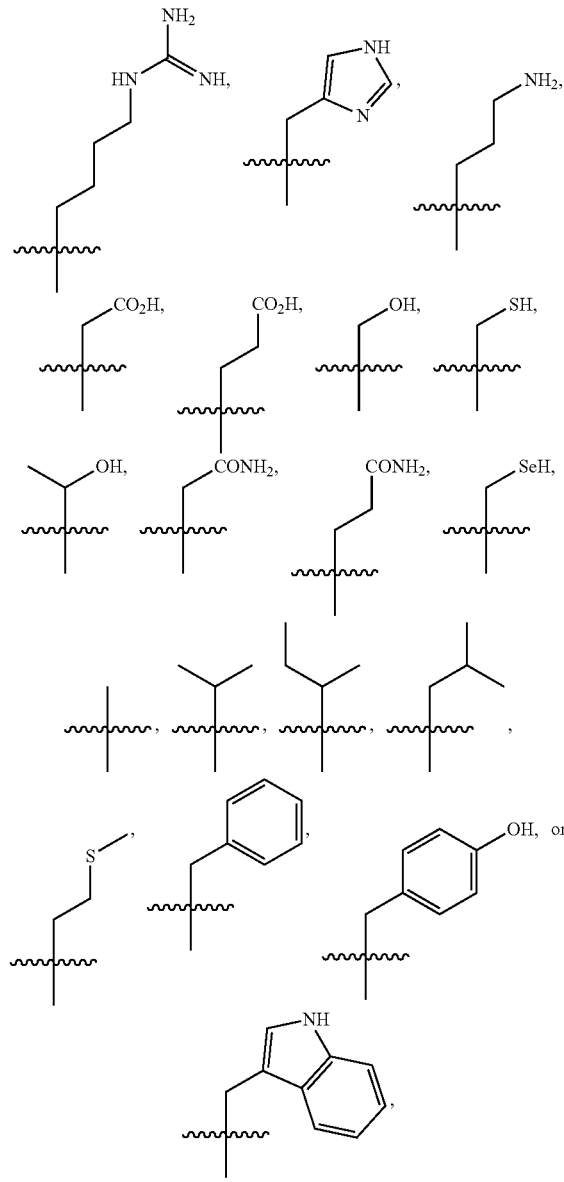

and R1 is the same at each gamma carbon.

36. A composition comprising the compound of claim 24, and a transfection reagent.

37. The composition of claim 36, which the transfection agent is a liposome.

38. A kit comprising the composition of claim 24 in a vessel.

39. The kit of claim 38, further comprising a transfection reagent.

40. The method of claim 1, wherein,
each instance of R1 is attached to a gamma carbon, and independently is selected from the group consisting of H,

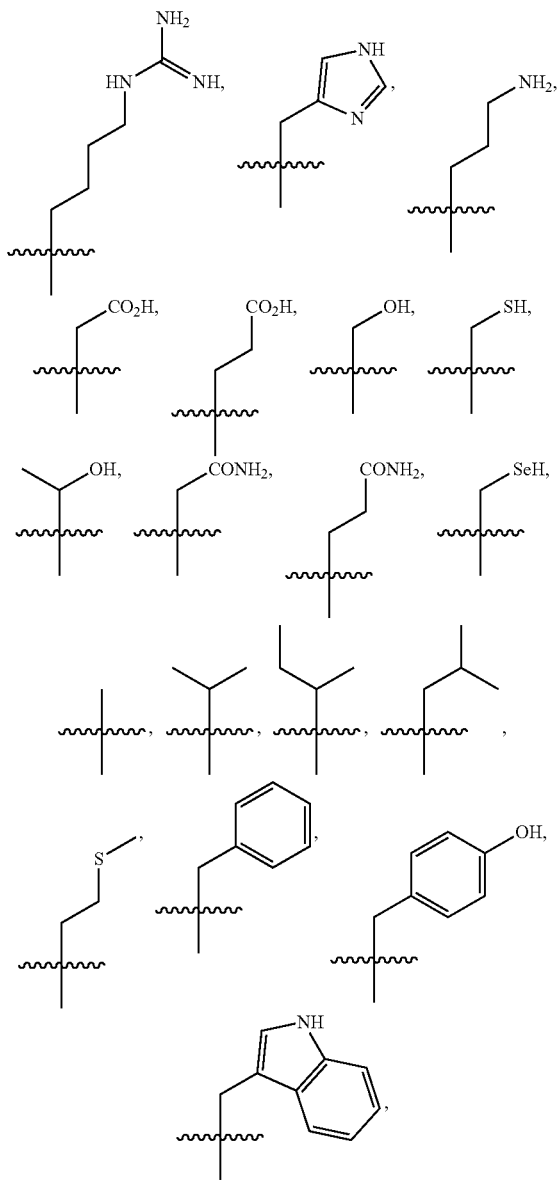

—CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$—O)$_q$—SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where P$_1$ is H;

q is an integer from 0 to 50, inclusive;

r and s are each independently integers from 1 to 50, inclusive; and

R2 is H, or

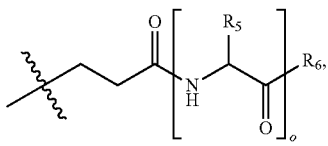

where o is 1-20, each instance of R5 is, independently

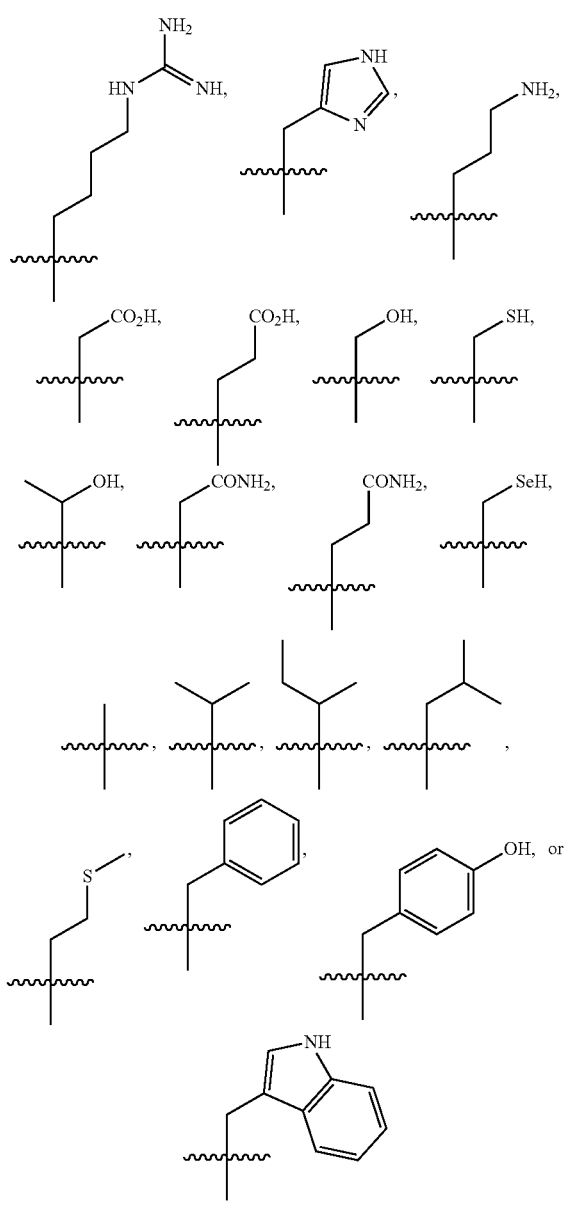

and R6 is —OH or NH₂.

41. The composition of claim 24, wherein, each instance of R1 is attached to a gamma carbon, and independently is selected from the group consisting of H,

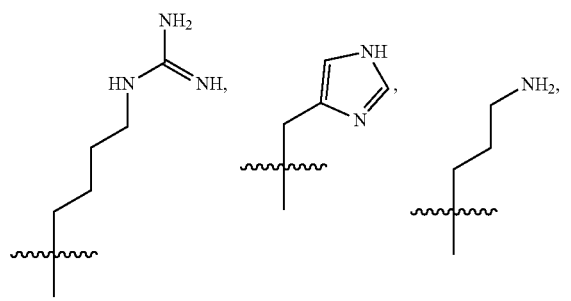

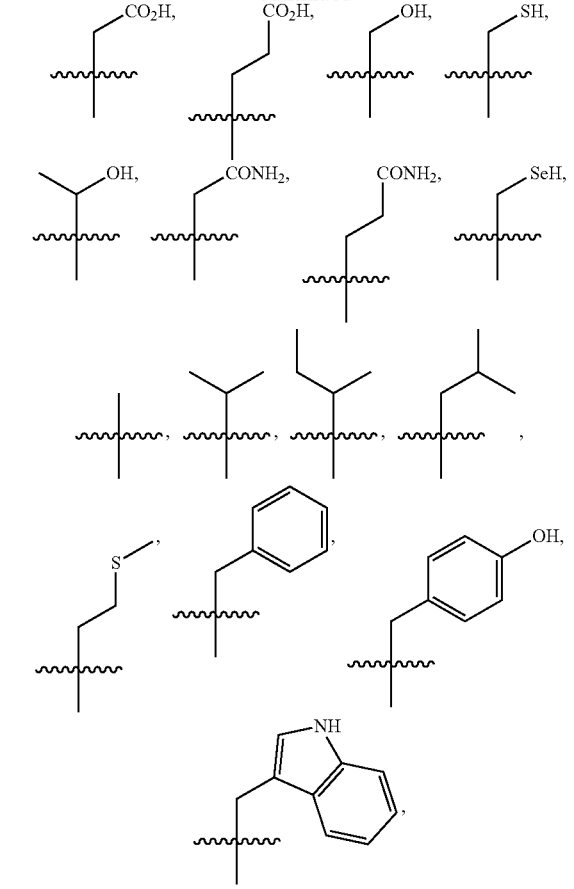

—CH₂—(OCH₂—CH₂)$_q$OP₁, —CH₂—(OCH₂—CH₂)$_q$—NHP₁, —CH₂—(OCH₂—CH₂—O)$_q$—SP₁ and —CH₂—(SCH₂—CH₂)$_q$—SP₁, —CH₂—(OCH₂—CH₂)$_r$—OH, —CH₂—(OCH₂—CH₂)$_r$—NH₂, —CH₂—(OCH₂—CH₂)$_r$—NHC(NH)NH₂, or —CH₂—(OCH₂—CH₂)$_r$—S—S[CH₂CH₂]$_s$NHC(NH)NH₂, where P₁ is H;

q is an integer from 0 to 50, inclusive;

r and s are each independently integers from 1 to 50, inclusive; and

R2 is H, or

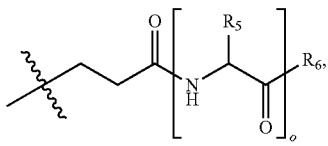

where o is 1-20, each instance of R5 is, independently

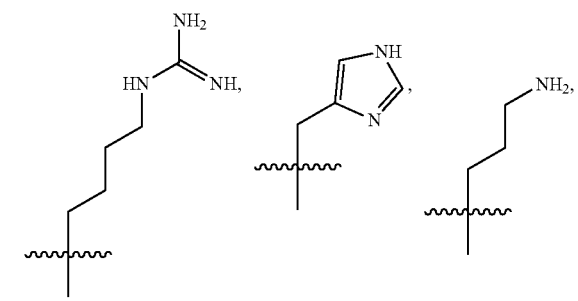

-continued

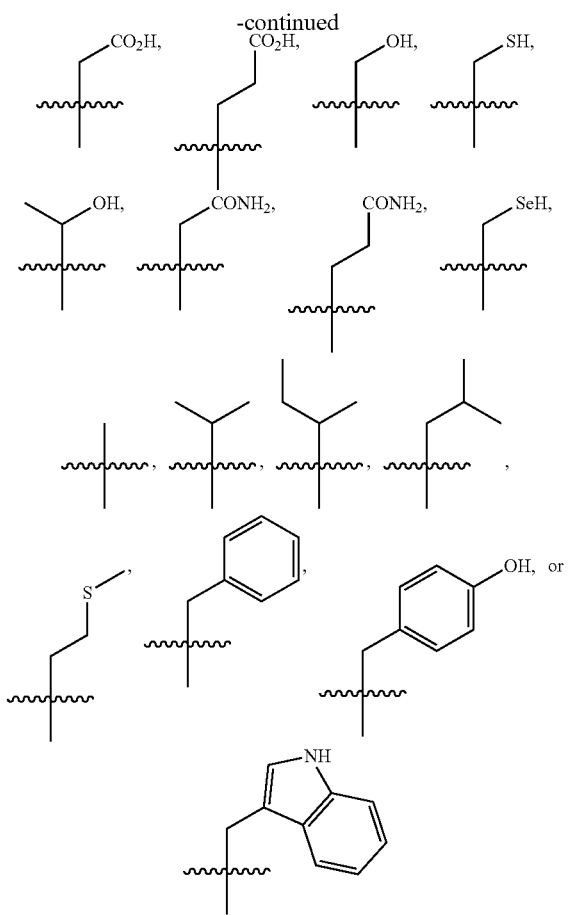

and R6 is —OH or NH$_2$.

42. The method of claim 1, in which the sequence of nucleobases R for the recognition modules is, from 5' to 3': GAA, or a sequence complementary thereto.

43. The method of claim 1, in which the sequence of nucleobases R for the recognition modules is, from 5' to 3': CGG, or a sequence complementary thereto.

44. The method of claim 1, in which the sequence of nucleobases R for the recognition modules is, from 5' to 3': CCG, or a sequence complementary thereto.

45. The method of claim 1, in which the sequence of nucleobases R for the recognition modules is, from 5' to 3': CAG, or a sequence complementary thereto.

46. The method of claim 1, in which the sequence of nucleobases R for the recognition modules is, from 5' to 3': CTG, or a sequence complementary thereto.

47. The method of claim 1, in which the sequence of nucleobases R for the recognition modules is, from 5' to 3': CCTG, or a sequence complementary thereto.

48. The method of claim 1, in which the sequence of nucleobases R for the recognition modules is, from 5' to 3': ATTCT, or a sequence complementary thereto.

49. The method of claim 1, in which the sequence of nucleobases R for the recognition modules is, from 5' to 3': GGGGCC, or a sequence complementary thereto.

50. The composition of claim 24, in which the sequence of nucleobases R for the recognition modules is, from 5' to 3': GAA, or a sequence complementary thereto.

51. The composition of claim 24, in which the sequence of nucleobases R for the recognition modules is, from 5' to 3': CGG, or a sequence complementary thereto.

52. The composition of claim 24, in which the sequence of nucleobases R for the recognition modules is, from 5' to 3': CCG, or a sequence complementary thereto.

53. The composition of claim 24, in which the sequence of nucleobases R for the recognition modules is, from 5' to 3': CAG, or a sequence complementary thereto.

54. The composition of claim 24, in which the sequence of nucleobases R for the recognition modules is, from 5' to 3': CTG, or a sequence complementary thereto.

55. The composition of claim 24, in which the sequence of nucleobases R for the recognition modules is, from 5' to 3': CCTG, or a sequence complementary thereto.

56. The composition of claim 24, in which the sequence of nucleobases R for the recognition modules is, from 5' to 3': ATTCT, or a sequence complementary thereto.

57. The composition of claim 24, in which the sequence of nucleobases R for the recognition modules is, from 5' to 3': GGGGCC, or a sequence complementary thereto.

* * * * *

UNITED STATES PATENT AND TRADEMARK OFFICE
CERTIFICATE OF CORRECTION

PATENT NO. : 10,221,216 B2  
APPLICATION NO. : 14/782448  
DATED : March 5, 2019  
INVENTOR(S) : Danith H. Ly et al.

Page 1 of 1

It is certified that error appears in the above-identified patent and that said Letters Patent is hereby corrected as shown below:

On the Title Page

Column 1, Line 5, delete "Rapireddy Srinivas," and insert -- Srinivas Rapireddy, --

In the Claims

Column 25, Line 1, Claim 1, delete "or" and insert -- of --

Column 27, Line 6, Claim 1, delete "instant" and insert -- instance --

Column 27, Line 56, Claim 11, delete "–S–R7," and insert -- –S–S–R7, --

Column 30, Line 11, Claim 12, delete "is" and insert -- is, --

Column 30, Line 11, Claim 12, delete "nucleobases." and insert -- nucleobase. --

Column 32, Line 65-66, Claim 18, delete "R of both" and insert -- R --

Column 36, Line 16, Claim 27, delete "–S–R7," and insert -- –S–S–R7, --

Column 42, Line 26, Claim 33, delete "or" and insert -- of --

Column 43, Line 62, Claim 37, delete "36," and insert -- 36, in --

Column 46, Line 38, Claim 41, delete "SP$_1$and" and insert -- SP$_1$ and --

Column 43, Line 60, Claim 36, delete "compound" and insert -- composition --

Signed and Sealed this  
Twenty-eighth Day of January, 2020

Andrei Iancu  
*Director of the United States Patent and Trademark Office*